US012655479B2

(12) United States Patent
Kermekchiev et al.

(10) Patent No.: US 12,655,479 B2
(45) Date of Patent: Jun. 16, 2026

(54) FAST AND ROBUST BI-FUNCTIONAL MUTANTS OF TAQ DNA POLYMERASE

(71) Applicant: DNA POLYMERASE TECHNOLOGY, INC., St. Louis, MO (US)

(72) Inventors: Milko B. Kermekchiev, St. Louis, MO (US); Zhian Zhang, Ballwin, MO (US)

(73) Assignee: DNA POLYMERASE TECHNOLOGY, INC., St. Louis, MO (US)

( * ) Notice: Subject to any disclaimer, the term of this patent is extended or adjusted under 35 U.S.C. 154(b) by 839 days.

(21) Appl. No.: 18/045,369

(22) Filed: Oct. 10, 2022

(65) Prior Publication Data

US 2023/0143626 A1     May 11, 2023

Related U.S. Application Data

(60) Provisional application No. 63/262,382, filed on Oct. 11, 2021.

(51) Int. Cl.
*C12Q 1/686*          (2018.01)
*C12N 9/12*           (2006.01)

(52) U.S. Cl.
CPC ........... *C12Q 1/686* (2013.01); *C12N 9/1241* (2013.01)

(58) Field of Classification Search
None
See application file for complete search history.

(56) References Cited

U.S. PATENT DOCUMENTS

| | | | |
|---|---|---|---|
| 5,436,149 A | 7/1995 | Barnes | |
| 5,436,326 A | 7/1995 | Ishino et al. | |
| 5,616,494 A | 4/1997 | Barnes | |
| 5,753,482 A | 5/1998 | Ishino et al. | |
| 5,928,866 A | 7/1999 | Imamoto et al. | |
| 6,210,885 B1 | 4/2001 | Gjerde et al. | |
| 6,395,526 B1 | 5/2002 | Uemori et al. | |
| 6,410,277 B1 | 6/2002 | Barnes | |
| 6,448,048 B1 | 9/2002 | Tomono et al. | |
| 7,211,647 B2 | 5/2007 | Ishino et al. | |
| 7,393,635 B2 | 7/2008 | Barnes | |
| 7,462,475 B2 | 12/2008 | Kermekchiev et al. | |
| 7,820,423 B2 | 10/2010 | Doi et al. | |
| 7,927,853 B2 | 4/2011 | Nishida et al. | |
| 8,003,346 B2 | 8/2011 | Tokida et al. | |
| 8,481,685 B2 | 7/2013 | Bourn et al. | |
| 9,796,965 B2 | 10/2017 | Kermekchiev et al. | |
| 10,683,537 B2 | 6/2020 | Kermekchiev et al. | |
| 11,091,745 B2 | 8/2021 | Barnes et al. | |
| 2004/0005594 A1 | 1/2004 | Holliger et al. | |
| 2004/0081963 A1 | 4/2004 | Wang | |
| 2005/0250131 A1 | 11/2005 | Jestin et al. | |
| 2006/0084074 A1 | 4/2006 | Kermekchiev et al. | |
| 2007/0020622 A1 | 1/2007 | Lee et al. | |

| | | | | |
|---|---|---|---|---|
| 2007/0048748 A1 | 3/2007 | Williams et al. | | |
| 2008/0014609 A1 | 1/2008 | Jestin et al. | | |
| 2008/0166772 A1 | 7/2008 | Hollinger et al. | | |
| 2009/0170060 A1 | 7/2009 | Kermekchiev et al. | | |
| 2011/0027832 A1 | 2/2011 | Kermekchiev et al. | | |
| 2011/0027833 A1 | 2/2011 | Hogrefe et al. | | |
| 2011/0142792 A1 | 6/2011 | Kahre et al. | | |
| 2011/0281305 A1 | 11/2011 | Bourn et al. | | |
| 2012/0028259 A1 | 2/2012 | Zhang et al. | | |
| 2012/0094332 A1 | 4/2012 | Lee et al. | | |
| 2013/0034879 A1 | 2/2013 | Skirgaila et al. | | |
| 2013/0040365 A1 | 2/2013 | Vander Horn et al. | | |
| 2013/0209473 A1 | 8/2013 | de Sauvage et al. | | |
| 2014/0186840 A1 | 7/2014 | Ding et al. | | |
| 2014/0322793 A1 | 10/2014 | Ishino et al. | | |
| 2014/0363875 A1 | 12/2014 | Ishino et al. | | |
| 2016/0304845 A1 | 10/2016 | Ishino et al. | | |
| 2018/0112195 A1* | 4/2018 | Barnes ................ C12Q 1/6846 |
| 2021/0147908 A1 | 5/2021 | Kermekchiev et al. | | |

FOREIGN PATENT DOCUMENTS

| | | | |
|---|---|---|---|
| JP | 2009136188 A | 6/2009 | |
| WO | 1992006200 A1 | 4/1992 | |
| WO | 2005113829 A2 | 12/2005 | |
| WO | 2010062777 A2 | 6/2010 | |
| WO | 2010062779 A2 | 6/2010 | |
| WO | 2012088479 A2 | 6/2012 | |
| WO | 2012110061 A1 | 8/2012 | |
| WO | 2016183294 A1 | 11/2016 | |

OTHER PUBLICATIONS

Lamble, S. Directed evolution of Thermus aquaticus DNA polymerase by compartmentalised self-replication. Dissertation, University of Bath, 2009. (Year: 2009).*

Appeal Brief in U.S. Appl. No. 16/901,101, mailed Dec. 14, 2022, 39 pages.

Barnes et al., "A Single Amino Acid Change to Taq DNA Polymerase Enables Faster PCR, Reverse Transcription and Strand-Displacement," Frontiers in Bioengineering and Biotechnology, Jan. 14, 2021, vol. 8, 10 pages.

Examiner's Answer in U.S. Appl. No. 16/901,101, mailed Mar. 14, 2023, 60 pages.

Final Reaction in U.S. Appl. No. 16/901,101, mailed Jun. 16, 2022, 56 pages.

(Continued)

*Primary Examiner* — Samuel C Woolwine

(74) *Attorney, Agent, or Firm* — McKee, Voorhees & Sease, PLC

(57)          ABSTRACT

Amino acid substitutions that provide for increased elongation rates, resistance to PCR inhibitors, and reverse transcriptase activity of *Thermus aquaticus* (Taq) DNA polymerase enzymes are provided. Also provided are related methods of using the Taq DNA polymerase enzymes to rapidly detect nucleic acids of interest in crude biological samples, without DNA/RNA extraction.

20 Claims, 20 Drawing Sheets

Specification includes a Sequence Listing.

(56) References Cited

OTHER PUBLICATIONS

Ghadessy et al., "Directed evolution of polymerase function by compartmentalized self-replication," Proceedings of the National Academy of Sciences, Apr. 10, 2001, vol. 98, No. 8, pp. 4552-4557.

Jonson et al., "A critical view on conservative mutations," Protein Engineering, Jun. 2001, vol. 14, No. 6, pp. 397-402.

Kermekchiev et al., "Cold-sensitive mutants of Taq DNA polymerase provide a hot start for PCR," Nucleic Acids Research, Nov. 1, 2003, vol. 31, No. 21, pp. 6139-6147.

Kermekchiev et al., "Mutants of Taq DNA polymerase resistant to PCR inhibitors allow DNA amplification from whole blood and crude soil samples," Nucleic Acids Research, Feb. 10, 2009, vol. 37, No. 5, 14 pages.

Lawyer et al., "High-level expression, purification, and enzymatic characterization of full-length Thermus aquaticus DNA polymerase and a truncated form deficient in 5' to 3' exonuclease activity," Genome Research, May 1993, vol. 2, No. 4, pp. 275-287.

Livingstone et al., "Protein sequence alignments: a strategy for the hierarchical analysis of residue conservation," Cabios, Dec. 1993, vol. 9, No. 6, pp. 745-756.

Reply Brief in U.S. Appl. No. 16/901,101, mailed May 12, 2023, 16 pages.

Third Party Submission in U.S. Appl. No. 16/901,101, mailed Jun. 9, 2021, 17 pages.

Wu et al., "A conservative isoleucine to leucine mutation causes major rearrangements and cold sensitivity in KlenTaq1 DNA polymerase," Biochemistry, Jan. 27, 2015, vol. 54, pp. 881-889.

* cited by examiner

SEQUENCE LISTING

```
Sequence total quantity: 20
SEQ ID NO: 1              moltype = AA  length = 832
FEATURE                  Location/Qualifiers
source                   1..832
                         mol_type = protein
                         organism = Thermus aquaticus
SEQUENCE: 1
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KE          832

SEQ ID NO: 2              moltype = AA  length = 554
FEATURE                  Location/Qualifiers
source                   1..554
                         mol_type = protein
                         organism = synthetic construct
SEQUENCE: 2
MVLLHEFGLL ESPKALEEAP WPPPEGAFVG FVLSRKEPMW ADLLALAAAR GGRVHRAPEP   60
YKALRDLKEA RGLLAKDLSV LALREGLGLP PGDDPMLLAY LLDPSNTTPE GVARRYGGEW  120
TEEAGERAAL SERLFANLWG RLEGEERLLW LYREVERPLS AVLAHMEATG VRLDVAYLRA  180
LSLEVAEEIA RLEAEVFRLA GHPFNLNSRD QLERVLFDEL GLPAIGKTEK TGKRSTSAAV  240
LEALREAHPI VEKILQYREL TKLKSTYIDP LPDLIHPRTG RLHTRFNQTA TATGRLSSSD  300
PNLQNIPVRT PLGQRIRRAF IAEEGWLLVA LDYSQIELRV LAHLSGDENL IRVFQEGRDI  360
HTETASWMFG VPREAVDPLM RRAAKTINFG VLYGMSAHRL SQELAIPYEE AQAFIERYFQ  420
SFPKVRAWIE KTLEEGRRRG YVETLFGRRR YVPDLEARVK SVREAAERMA FNMPVQGTAA  480
DLMKLAMVKL FPRLEEMGAR MLLQVHDELV LEAPKERAEA VARLAKEVME GVYPLAVPLE  540
VEVGIGEDWL SAKE                                                    554

SEQ ID NO: 3              moltype = AA  length = 832
FEATURE                  Location/Qualifiers
source                   1..832
                         mol_type = protein
                         organism = synthetic construct
SEQUENCE: 3
MRGMLPLFEP KGRVLLVDGH HLAYRTFHAL KGLTTSRGEP VQAVYGFAKS LLKALKEDGD   60
```

```
AVIVVFDAKA PSFRHEAYGG YKAGRAPTPE DFPRQLALIK ELVDLLGLAR LEVPGYEADD    120
VLASLAKKAE KEGYEVRILT ADKDLYQLLS DRIHVLHPEG YLITPAWLWE KYGLRPDQWA    180
DYRALTGDES DNLPGVKGIG EKTARKLLEE WGSLEALLKN LDRLKPAIRE KILAHMDDLK    240
LSWDLAKVRT DLPLEVDFAK RREPDRERLR AFLERLEFGS LLHEFGLLES PKALEEAPWP    300
PPEGAFVGFV LSRKEPMWAD LLALAAARGG RVHRAPEPYK ALRDLKEARG LLAKDLSVLA    360
LREGLGLPPG DDPMLLAYLL DPSNTTPEGV TRRYGGEWTE EAGERAALSE RLFANLWGRL    420
EGEERLLWLY REVERPLSAV LAHMEATGVR LDVAYLRALS LEVAEEIARL EAEVFRLAGH    480
PFNLNSRDQL ERVLFDELGL PAIGKTEKTG KRSTSAAVLE ALREAHPIVE KILQYRELTK    540
LKSTYIDPLP DLIHPRTGRL HTRFNQTATA TGRLSSSDPN LQNIPVRTPL GQRIRRAFIA    600
EEGWLLVALD YSQIELRVLA HLSGDENLIR VFQEGRDIHT ETASWMFGVP REAVDPLMRR    660
AAKTINFGVL YGMSAHRLSQ ELAIPYEEAQ AFIERYFQSF PKVRAWIEKT LEEGRRRGYV    720
ETLFGRRRYV PNLEARVKSV RRRAERMAFN MSVQGTAADL MKLAMVKLFP RLEEMGARML    780
LQVHDELVLE APKERAEAVA RLAKEVMEGV YPLAVPLVVE VGIGEDWLSA KE           832
```

```
SEQ ID NO: 4              moltype = AA  length = 832
FEATURE                   Location/Qualifiers
source                    1..832
                          mol_type = protein
                          organism = synthetic construct
SEQUENCE: 4
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD    120
VLASLAKKAE KEGYEVRILT ADKDLYQLLS DRIHVLHPEG YLITPAWLWE KYGLRPDQWA    180
DYRALTGDES DNLPGVKGIG EKTARKLLEE WGSLEALLKN LDRLKPAIRE KILAHMDDLK    240
LSWDLAKVRT DLPLEVDFAK RREPDRERLR AFLERLEFGS LLHEFGLLES PKALEEAPWP    300
PPEGAFVGFV LSRKEPMWAD LLALAAARGG RVHRAPEPYK ALRDLKEARG LLAKDLSVLA    360
LREGLGLPPG DDPMLLAYLL DPSNTTPEGV ARRYGGEWTE EAGERAALSE RLFANLWGRL    420
EGEERLLWLY REVERPLSAV LAHMEATGVR LDVAYLRALS LEVAEEIARL EAEVFRLAGH    480
PFNLNSRDQL ERVLFDELGL PAIGKTEKTG KRSTSAAVLE ALREAHPIVE KILQYRELTK    540
LKSTYIDPLP DLIHPRTGRL HTRFNQTATA TGRLSSSDPN LQNIPVRTPL GQRIRRAFIA    600
EEGWLLVALD YSQIELRVLA HLSGDENLIR VFQEGRDIHT ETASWMFGVP REAVDPLMRR    660
AAKTINFGVL YGMSAHRLSQ ELAIPYEEAQ AFIERYFQSF PKVRAWIEKT LEEGRRRGYV    720
ETLFGRRRYV PKLEARVKSV RKRAERMAFN MPVQGTAADL MKLAMVKLFP RLEEMGARML    780
LQVHDELVLE APKERAEAVA RLAKEVMEGV YPLAVPLEVE VGIGEDWLSA KE           832
```

```
SEQ ID NO: 5              moltype = AA  length = 832
FEATURE                   Location/Qualifiers
source                    1..832
                          mol_type = protein
                          organism = synthetic construct
SEQUENCE: 5
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD    120
VLASLAKKAE KEGYEVRILT ADKDLYQLLS DRIHVLHPEG YLITPAWLWE KYGLRPDQWA    180
DYRALTGDES DNLPGVKGIG EKTARKLLEE WGSLEALLKN LDRLKPAIRE KILAHMDDLK    240
LSWDLAKVRT DLPLEVDFAK RREPDRERLR AFLERLEFGS LLHEFGLLES PKALEEAPWP    300
PPEGAFVGFV LSRKEPMWAD LLALAAARGG RVHRAPEPYK ALRDLKEARG LLAKDLSVLA    360
LREGLGLPPG DDPMLLAYLL DPSNTTPEGV ARRYGGEWTE EAGERAALSE RLFANLWGRL    420
EGEERLLWLY REVERPLSAV LAHMEATGVR LDVAYLRALS LEVAEEIARL EAEVFRLAGH    480
PFNLNSRDQL ERVLFDELGL PAIGKTEKTG KRSTSAAVLE ALREAHPIVE KILQYRELTK    540
LKSTYIDPLP DLIHPRTGRL HTRFNQTATA TGRLSSSDPN LQNIPVRTPL GQRIRRAFIA    600
EEGWLLVALD YSQIELRVLA HLSGDENLIR VFQEGRDIHT ETASWMFGVP REAVDPLMRR    660
AAKTINFGVL YGMSAHRLSQ ELAIPYEEAQ AFIERYFQSF PKVRAWIEKT LEEGRRRGYV    720
ETLFGRRRYV PNLEARVKSV RRRAERMAFN MSVQGTAADL MKLAMVKLFP RLEEMGARML    780
LQVHDELVLE APKERAEAVA RLAKEVMEGV YPLAVPLVVE VGIGEDWLSA KE           832
```

```
SEQ ID NO: 6              moltype = AA  length = 832
FEATURE                   Location/Qualifiers
source                    1..832
                          mol_type = protein
                          organism = synthetic construct
SEQUENCE: 6
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD    120
VLASLAKKAE KEGYEVRILT ADKDLYQLLS DRIHVLHPEG YLITPAWLWE KYGLRPDQWA    180
DYRALTGDES DNLPGVKGIG EKTARKLLEE WGSLEALLKN LDRLKPAIRE KILAHMDDLK    240
LSWDLAKVRT DLPLEVDFAK RREPDRERLR AFLERLEFGS LLHEFGLLES PKALEEAPWP    300
PPEGAFVGFV LSRKEPMWAD LLALAAARGG RVHRAPEPYK ALRDLKEARG LLAKDLSVLA    360
LREGLGLPPG DDPMLLAYLL DPSNTTPEGV ARRYGGEWTE EAGERAALSE RLFANLWGRL    420
EGEERLLWLY REVERPLSAV LAHMEATGVR LDVAYLRALS LEVAEEIARL EAEVFRLAGH    480
PFNLNSRDQL ERVLFDELGL PAIGKTEKTG KRSTSAAVLE ALREAHPIVE KILQYRELTK    540
LKSTYIDPLP DLIHPRTGRL HTRFNQTATA TGRLSSSDPN LQNIPVRTPL GQRIRRAFIA    600
EEGWLLVALD YSQIELRVLA HLSGDENLIR VFQEGRDIHT ETASWMFGVP REAVDPLMRR    660
AAKTINFGVL YGMSAHRLSQ ELAIPYEEAQ AFIERYFQSF PKVRAWIEKT LEEGRRRGYV    720
ETLFGRRRYV PNLEARVRSV RRRAERMAFN MPVQGTAADL MKLAMVKLFP RLEEMGARML    780
LQVHDELVLE APKERAEAVA RLAKEVMEGV YPLAVPLEVE VGIGEDWLSA KE           832
```

```
SEQ ID NO: 7              moltype = AA  length = 832
FEATURE                   Location/Qualifiers
```

```
source                1..832
                      mol_type = protein
                      organism = synthetic construct
SEQUENCE: 7
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PNLEARVKSV RRRAERMAFN MPVQGTAADL MKLAMVKLFP RLEEMGARML   780
LQVHDELVLE APKERAEAVA RLAKEVMEGV YPLTVPLEVE VGIGEDWLSA KE            832

SEQ ID NO: 8         moltype = AA   length = 832
FEATURE              Location/Qualifiers
source               1..832
                     mol_type = protein
                     organism = synthetic construct
SEQUENCE: 8
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PNLEARVKSV RRRAERMAFN MPVQGTAADL MKLAMVKLFP RLEEMGARML   780
LQVHDELVLE APKERAEAVA RLAKEVMEGV YPLAVPLVVE VGIGEDWLSA KE            832

SEQ ID NO: 9         moltype = AA   length = 832
FEATURE              Location/Qualifiers
source               1..832
                     mol_type = protein
                     organism = synthetic construct
SEQUENCE: 9
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV TRRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KE            832

SEQ ID NO: 10        moltype = AA   length = 832
FEATURE              Location/Qualifiers
source               1..832
                     mol_type = protein
                     organism = synthetic construct
SEQUENCE: 10
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
```

```
ETLFGRRRYV PDLEARVKSV REAAERMAFN MSVQGTAADL MKLAMVKLFP RLEEMGARML   780
LQVHDELVLE APKERAEAVA RLAKEVMEGV YPLAVPLEVE VGIGEDWLSA KE            832

SEQ ID NO: 11            moltype = AA   length = 832
FEATURE                  Location/Qualifiers
source                   1..832
                         mol_type = protein
                         organism = synthetic construct
SEQUENCE: 11
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLTVPLEVE VGIGEDWLSA KE           832

SEQ ID NO: 12            moltype = AA   length = 554
FEATURE                  Location/Qualifiers
source                   1..554
                         mol_type = protein
                         organism = synthetic construct
SEQUENCE: 12
MVLLHEFGLL ESPKALEEAP WPPPEGAFVG FVLSRKEPMW ADLLALAAAR GGRVHRAPEP   60
YKALRDLKEA RGLLAKDLSV LALREGLGLP PGDDPMLLAY LLDPSNTTPE GVTRRYGGEW  120
TEEAGERAAL SERLFANLWG RLEGEERLLW LYREVERPLS AVLAHMEATG VRLDVAYLRA  180
LSLEVAEEIA RLEAEVFRLA GHPFNLNSRD QLERVLFDEL GLPAIGKTEK TGKRSTSAAV  240
LEALREAHPI VEKILQYREL TKLKSTYIDP LPDLIHPRTG RLHTRFNQTA TATGRLSSSD  300
PNLQNIPVRT PLGQRIRRAF IAEEGWLLVA LDYSQIELRV LAHLSGDENL IRVFQEGRDI  360
HTETASWMFG VPREAVDPLM RRAAKTINFG VLYGMSAHRL SQELAIPYEE AQAFIERYFQ  420
SFPKVRAWIE KTLEEGRRRG YVETLFGRRR YVPNLEARVK SVRRRAERMA FNMSVQGTAA  480
DLMKLAMVKL FPRLEEMGAR MLLQVHDELV LEAPKERAEA VARLAKEVME GVYPLAVPLV  540
VEVGIGEDWL SAKE                                                    554

SEQ ID NO: 13            moltype = AA   length = 554
FEATURE                  Location/Qualifiers
source                   1..554
                         mol_type = protein
                         organism = synthetic construct
SEQUENCE: 13
MVLLHEFGLL ESPKALEEAP WPPPEGAFVG FVLSRKEPMW ADLLALAAAR GGRVHRAPEP   60
YKALRDLKEA RGLLAKDLSV LALREGLGLP PGDDPMLLAY LLDPSNTTPE GVARRYGGEW  120
TEEAGERAAL SERLFANLWG RLEGEERLLW LYREVERPLS AVLAHMEATG VRLDVAYLRA  180
LSLEVAEEIA RLEAEVFRLA GHPFNLNSRD QLERVLFDEL GLPAIGKTEK TGKRSTSAAV  240
LEALREAHPI VEKILQYREL TKLKSTYIDP LPDLIHPRTG RLHTRFNQTA TATGRLSSSD  300
PNLQNIPVRT PLGQRIRRAF IAEEGWLLVA LDYSQIELRV LAHLSGDENL IRVFQEGRDI  360
HTETASWMFG VPREAVDPLM RRAAKTINFG VLYGMSAHRL SQELAIPYEE AQAFIERYFQ  420
SFPKVRAWIE KTLEEGRRRG YVETLFGRRR YVPKLEARVK SVRKRAERMA FNMPVQGTAA  480
DLMKLAMVKL FPRLEEMGAR MLLQVHDELV LEAPKERAEA VARLAKEVME GVYPLAVPLE  540
VEVGIGEDWL SAKE                                                    554

SEQ ID NO: 14            moltype = AA   length = 554
FEATURE                  Location/Qualifiers
source                   1..554
                         mol_type = protein
                         organism = synthetic construct
SEQUENCE: 14
MVLLHEFGLL ESPKALEEAP WPPPEGAFVG FVLSRKEPMW ADLLALAAAR GGRVHRAPEP   60
YKALRDLKEA RGLLAKDLSV LALREGLGLP PGDDPMLLAY LLDPSNTTPE GVARRYGGEW  120
TEEAGERAAL SERLFANLWG RLEGEERLLW LYREVERPLS AVLAHMEATG VRLDVAYLRA  180
LSLEVAEEIA RLEAEVFRLA GHPFNLNSRD QLERVLFDEL GLPAIGKTEK TGKRSTSAAV  240
LEALREAHPI VEKILQYREL TKLKSTYIDP LPDLIHPRTG RLHTRFNQTA TATGRLSSSD  300
PNLQNIPVRT PLGQRIRRAF IAEEGWLLVA LDYSQIELRV LAHLSGDENL IRVFQEGRDI  360
HTETASWMFG VPREAVDPLM RRAAKTINFG VLYGMSAHRL SQELAIPYEE AQAFIERYFQ  420
SFPKVRAWIE KTLEEGRRRG YVETLFGRRR YVPNLEARVK SVRRRAERMA FNMSVQGTAA  480
DLMKLAMVKL FPRLEEMGAR MLLQVHDELV LEAPKERAEA VARLAKEVME GVYPLAVPLV  540
VEVGIGEDWL SAKE                                                    554

SEQ ID NO: 15            moltype = AA   length = 554
FEATURE                  Location/Qualifiers
source                   1..554
                         mol_type = protein
```

-continued

```
                                organism = synthetic construct
SEQUENCE: 15
MVLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDENL IRVFQEGRDI   360
HTETASWMFG VPREAVDPLM RRAAKTINFG VLYGMSAHRL SQELAIPYEE AQAFIERYFQ   420
SFPKVRAWIE KTLEEGRRRG YVETLFGRRR YVPNLEARVR SVRRRAERMA FNMPVQGTAA   480
DLMKLAMVKL FPRLEEMGAR MLLQVHDELV LEAPKERAEA VARLAKEVME GVYPLAVPLE   540
VEVGIGEDWL SAKE                                                    554

SEQ ID NO: 16          moltype = AA  length = 554
FEATURE                Location/Qualifiers
source                 1..554
                       mol_type = protein
                       organism = synthetic construct
SEQUENCE: 16
MVLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDENL IRVFQEGRDI   360
HTETASWMFG VPREAVDPLM RRAAKTINFG VLYGMSAHRL SQELAIPYEE AQAFIERYFQ   420
SFPKVRAWIE KTLEEGRRRG YVETLFGRRR YVPNLEARVK SVRRRAERMA FNMPVQGTAA   480
DLMKLAMVKL FPRLEEMGAR MLLQVHDELV LEAPKERAEA VARLAKEVME GVYPLTVPLE   540
VEVGIGEDWL SAKE                                                    554

SEQ ID NO: 17          moltype = AA  length = 554
FEATURE                Location/Qualifiers
source                 1..554
                       mol_type = protein
                       organism = synthetic construct
SEQUENCE: 17
MVLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDENL IRVFQEGRDI   360
HTETASWMFG VPREAVDPLM RRAAKTINFG VLYGMSAHRL SQELAIPYEE AQAFIERYFQ   420
SFPKVRAWIE KTLEEGRRRG YVETLFGRRR YVPNLEARVK SVRRRAERMA FNMPVQGTAA   480
DLMKLAMVKL FPRLEEMGAR MLLQVHDELV LEAPKERAEA VARLAKEVME GVYPLAVPLV   540
VEVGIGEDWL SAKE                                                    554

SEQ ID NO: 18          moltype = AA  length = 554
FEATURE                Location/Qualifiers
source                 1..554
                       mol_type = protein
                       organism = synthetic construct
SEQUENCE: 18
MVLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVTRRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDENL IRVFQEGRDI   360
HTETASWMFG VPREAVDPLM RRAAKTINFG VLYGMSAHRL SQELAIPYEE AQAFIERYFQ   420
SFPKVRAWIE KTLEEGRRRG YVETLFGRRR YVPDLEARVK SVREAAERMA FNMPVQGTAA   480
DLMKLAMVKL FPRLEEMGAR MLLQVHDELV LEAPKERAEA VARLAKEVME GVYPLAVPLE   540
VEVGIGEDWL SAKE                                                    554

SEQ ID NO: 19          moltype = AA  length = 554
FEATURE                Location/Qualifiers
source                 1..554
                       mol_type = protein
                       organism = synthetic construct
SEQUENCE: 19
MVLLHEFGLL ESPKALEEAP WPPPEGAFVG FVLSRKEPMW ADLLALAAAR GGRVHRAPEP    60
YKALRDLKEA RGLLAKDLSV LALREGLGLP PGDDPMLLAY LLDPSNTTPE GVARRYGGEW   120
TEEAGERAAL SERLFANLWG RLEGEERLLW LYREVERPLS AVLAHMEATG VRLDVAYLRA   180
LSLEVAEEIA RLEAEVFRLA GHPFNLNSRD QLERVLFDEL GLPAIGKTEK TGKRSTSAAV   240
LEALREAHPI VEKILQYREL TKLKSTYIDP LPDLIHPRTG RLHTRFNQTA TATGRLSSSD   300
PNLQNIPVRT PLGQRIRRAF IAEEGWLLVA LDYSQIELRV LAHLSGDENL IRVFQEGRDI   360
HTETASWMFG VPREAVDPLM RRAAKTINFG VLYGMSAHRL SQELAIPYEE AQAFIERYFQ   420
SFPKVRAWIE KTLEEGRRRG YVETLFGRRR YVPDLEARVK SVREAAERMA FNMSVQGTAA   480
DLMKLAMVKL FPRLEEMGAR MLLQVHDELV LEAPKERAEA VARLAKEVME GVYPLAVPLE   540
```

-continued

```
VEVGIGEDWL SAKE                                                      554

SEQ ID NO: 20          moltype = AA  length = 554
FEATURE                Location/Qualifiers
source                 1..554
                       mol_type = protein
                       organism = synthetic construct
SEQUENCE: 20
MVLLHEFGLL ESPKALEEAP WPPPEGAFVG FVLSRKEPMW ADLLALAAAR GGRVHRAPEP  60
YKALRDLKEA RGLLAKDLSV LALREGLGLP PGDDPMLLAY LLDPSNTTPE GVARRYGGEW  120
TEEAGERAAL SERLFANLWG RLEGEERLLW LYREVERPLS AVLAHMEATG VRLDVAYLRA  180
LSLEVAEEIA RLEAEVFRLA GHPFNLNSRD QLERVLFDEL GLPAIGKTEK TGKRSTSAAV  240
LEALREAHPI VEKILQYREL TKLKSTYIDP LPDLIHPRTG RLHTRFNQTA TATGRLSSSD  300
PNLQNIPVRT PLGQRIRRAF IAEEGWLLVA LDYSQIELRV LAHLSGDENL IRVFQEGRDI  360
HTETASWMFG VPREAVDPLM RRAAKTINFG VLYGMSAHRL SQELAIPYEE AQAFIERYFQ  420
SFPKVRAWIE KTLEEGRRRG YVETLFGRRR YVPDLEARVK SVREAAERMA FNMPVQGTAA  480
DLMKLAMVKL FPRLEEMGAR MLLQVHDELV LEAPKERAEA VARLAKEVME GVYPLTVPLE  540
VEVGIGEDWL SAKE                                                      554
```

FAST AND ROBUST BI-FUNCTIONAL MUTANTS OF TAQ DNA POLYMERASE

CROSS-REFERENCE TO RELATED APPLICATIONS

This application claims priority under 35 U.S.C. § 119 to provisional patent application U.S. Ser. No. 63/262,382, filed Oct. 11, 2021. The provisional patent application is herein incorporated by reference in its entirety, including without limitation, the specification, sequence listing, claims, and abstract, as well as any figures, tables, appendices, or drawings thereof.

STATEMENT REGARDING FEDERALLY SPONSORED RESEARCH

This invention was made with government support under Grant No. GM128532 awarded by the National Institutes of Health. The government has certain rights in this invention.

INCORPORATION OF SEQUENCE LISTING

The instant application contains Sequence Listings which have been submitted in XML format via Patent Center and are hereby incorporated by reference in their entirety. Said XML copy, created Sep. 29, 2022, is named "P13716US01_SequenceListing.xml" and is 32,058 bytes in size.

BACKGROUND

Known mutant polymerases include Omni Taq, i.e., FL-22 (as described in U.S. Patent Application Publication No. 2011/0027832) and Omni Klentaq, i.e., KlenTaq-10 (as described in U.S. Patent Application Publication No. 2006/0084074).

Known mutant polymerases and uses thereof are described in, for example, U.S. Pat. No. 7,462,475, issued 9 Dec. 2008; U.S. Patent Application Publication No. 20090170060, published 2 Jul. 2009; U.S. Patent Application Publication No. 2011/0027832, published 3 Feb. 2011; U.S. Patent Application Publication No. 2012/0028259, published 2 Feb. 2012; and international PCT application WO2012/088479, published 28 Jun. 2012. Known mutant polymerases and uses thereof are also described in U.S. Patent Application Publication No. 2013/0040365, published 14 Feb. 2013; U.S. Pat. No. 10,683,537, issued Jun. 16, 2020; and U.S. Pat. No. 11,091,745, issued Aug. 17, 2021.

SUMMARY

DNA polymerases comprising a polypeptide sequence having at least 95% sequence identity to positions 279 through 832 of SEQ ID NO: 1, and further comprising one or more amino acid substitution selected from the group consisting of A391T, P752S, A814T, and combinations thereof, wherein all amino acid substitutions are relative to SEQ ID NO: 1 are provided. In certain embodiments, the DNA polymerases further comprise one or more amino acid substitutions selected from the group consisting of D732N, D732R, D732K, K738R, E742R, E742K, A743R, A743K, E818V, and combinations thereof, wherein all amino acid substitutions are relative to SEQ ID NO: 1. Recombinant DNA molecules comprising a polynucleotide encoding the DNA polymerases, optionally wherein a heterologous promoter is operably linked to the polynucleotide, are also provided. Cells comprising the recombinant DNA molecules are provided. Compositions comprising the DNA polymerases, optionally wherein the composition further comprises at least one of an anti-Taq antibody, an anti-Taq monoclonal antibody, an anti-Taq aptamer, or a buffering agent. Kits comprising the DNA polymerases, optionally wherein the kit further comprises at least one of a positive control template nucleic acid, positive control primer oligonucleotides which provide for polymerase chain reaction-mediated amplification of the positive control template, an anti-Taq antibody, an anti-Taq monoclonal antibody, and/or an anti-Taq aptamer are provided.

Methods of making the DNA polymerase comprising culturing a cell comprising a polynucleotide encoding the DNA polymerase and isolating the DNA polymerase from the cultured cells are provided.

Methods of amplifying a target nucleic acid in a polymerase chain reaction (PCR) comprising: forming an assay mixture comprising a sample comprising a target nucleic acid, primers specific for the target nucleic acid, a buffer, and at least one of the DNA polymerases; and amplifying the target nucleic acid in the assay mixture in a PCR to produce an amplification product are provided.

DESCRIPTION OF DRAWINGS

The drawings are not intended to limit the scope of the present disclosure in any way.

FIG. 1A shows amplification and FIG. 1B shows the melt peak. A 2 kb target from the pUC18 plasmid was amplified in real-time PCR in the presence of SYBR Green, with equivalent amounts of the mutant enzymes A777, F40, F44, and wild-type Taq. The amplification and melting curves are shown in FIG. 1A and FIG. 1B, correspondingly. Reactions contained 50 pg plasmid DNA and 0.5×SYBR Green. Two-step cycling was performed with a 10 sec/94 deg. denaturing step, followed by a 3 sec./62 deg. annealing/extension step, for 48 cycles. Under these conditions, when challenged with a very short extension time (3 sec for a 2 kb target), the three fast Taq mutants outperformed the plain Taq enzyme, and efficiently amplified the target with significantly lower Ct values (22-24, vs. 36 for Taq).

FIG. 2A shows amplification and FIG. 2B shows the melt peak. A 2 kb target from the pUC18 plasmid was amplified in real-time PCR in the presence of 0.5× SYBR Green, with equivalent amounts of the mutant enzymes A777, A555, and SpeedSTAR™ HS (SS-HS). The amplification and melting curves are shown in FIG. 2A and FIG. 2B, correspondingly. Reactions contained 50 pg plasmid DNA and 0.5×SYBR Green, and the PCR was performed in the reaction buffer recommended for the SpeedSTAR™ HS enzyme. Two-step cycling was performed with a 10 sec/94 deg. Denaturing step, followed by a 5 sec./62 deg. Annealing/extension step, for 48 cycles. Under these conditions, when challenged with a very short extension time (5 sec for a 2 kb target), the two fast Taq mutants outperformed the Takara fast enzyme, and efficiently amplified the target with significantly lower Ct values (Ct 4 and 18, vs. 24 for Takara SpeedSTAR™ HS).

FIG. 3A shows a 2 kb target of lambda phage DNA was amplified in real-time PCR with equivalent amounts of the Taq mutants A555, A777, or with the commercial SpeedSTAR™ Polymerase (SS-HS). Four two-fold dilutions were tested with each enzyme to amplify the target from 200 pg lambda DNA, in the presence of 0.5×SYBR Green. The real-time PCR melting curves (FIG. 3A) represent the reactions with the highest amount of enzyme. The reactions were performed in the buffer recommended for the SpeedSTAR™ (SS-HS) polymerase, in a two-step PCR, with 10 sec./94 deg and 1 sec./60 deg, for 48 cycles. The PCR products of the reactions (FIG. 3B) with the two highest amounts of each enzyme were resolved in an ethidium bromide stained 1.5% agarose gel, along with a DNA ladder (M). The specific PCR products are pointed by an arrow. FIG. 3C is as in 3A, but the target (1.8 kb) was from pUC18 plasmid DNA (20 pg DNA/reaction), amplified with another fast Taq mutant, G10, and commercial wild-type Taq Polymerase. The reactions were performed in the buffer recommended for the plain Taq polymerase. The selected fast Taq mutants were able to amplify both long targets with an impressive speed, upon extension time of 1 sec. (less than a second per kilobase), outperforming the two commercial enzymes. The PCR products of the reactions (FIG. 3D) with the two highest amounts of each enzyme were resolved in an ethidium bromide stained 1.5% agarose gel, along with a DNA ladder (M). The specific PCR products are pointed by an arrow.

FIG. 4A shows amplification, FIG. 4B shows the melt peak, and FIG. 4C shows an agarose gel. A 1.8 kb target from the pUC18 plasmid was amplified in real-time PCR in the presence of SYBR Green, with equivalent amounts of the mutant enzymes A555, A777, and SpeedSTAR™ (SS-HS) (4 two-fold dilutions each enzyme), in the presence of 5% human serum. The amplification and melting curves, representing the reactions with the highest amounts of each enzyme are shown in FIG. 4A and FIG. 4B, respectively, and an agarose gel image is shown in FIG. 4C. Reactions contained 35 pg plasmid DNA and 0.5×SYBR Green, and the PCR was performed in the reaction buffer recommended for the SpeedSTAR™ HS enzyme. Two-step cycling was performed with a 10 sec/94 deg. denaturing step, followed by a 2 sec./62 deg. annealing/extension step, for 48 cycles. The PCR products of the reactions with the two highest amounts of each enzyme were resolved in a 1.5% ethidium bromide stained agarose gel, along with a DNA ladder (lane M). The specific 1.8 kb PCR products are pointed by an arrow. The two fast Taq mutants outperformed the commercial SpeedSTAR™ HS fast enzyme, and efficiently amplified this 1.8 kb long target with only 2 sec extension time in the presence of serum, demonstrating their resistance to the known PCR inhibition by serum. The SS-HS polymerase failed to generate a specific PCR amplification product.

Figure 5A:
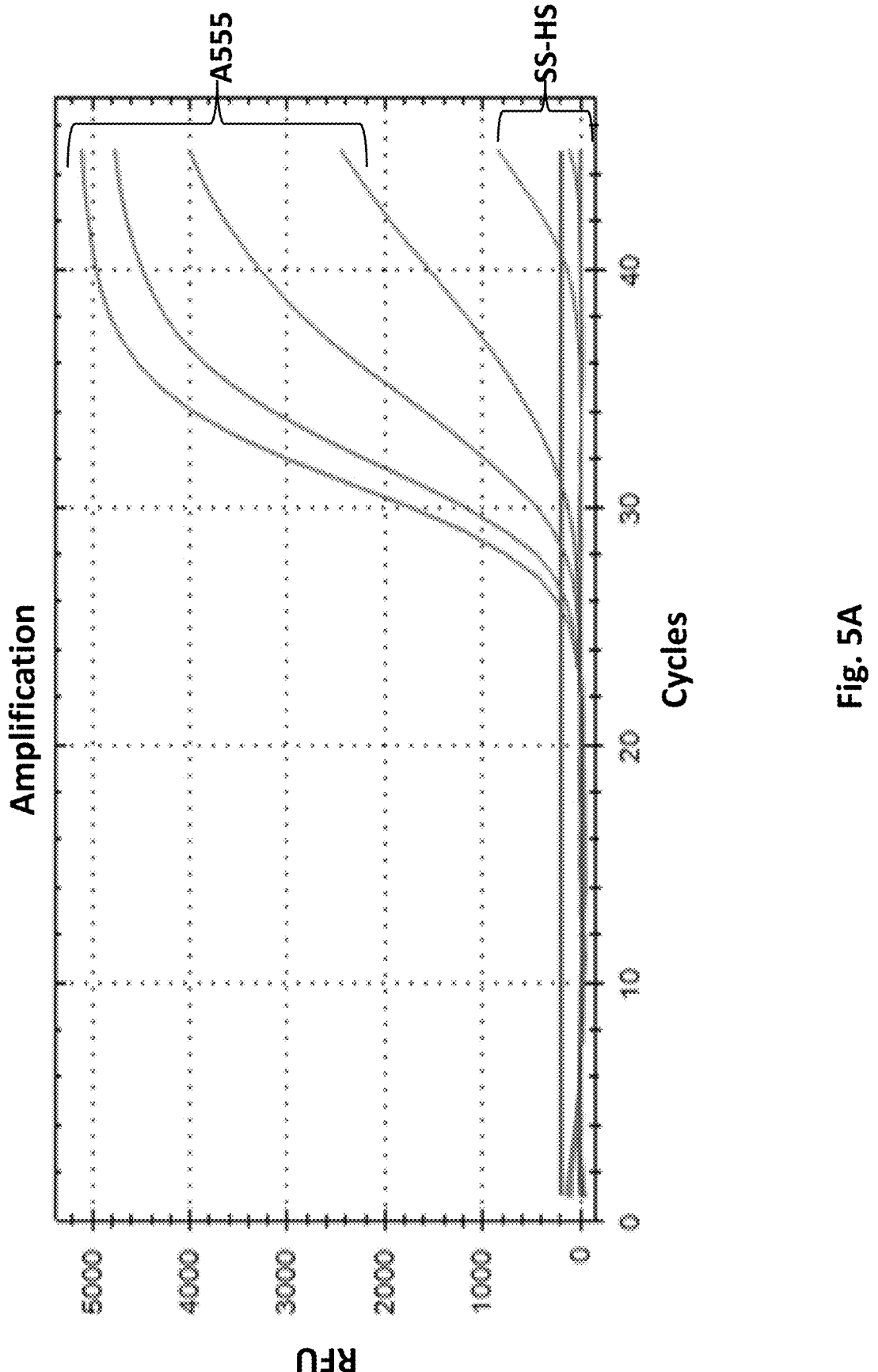
FIGS. 5A, 5B, and 5C show performance of the Taq mutant A555 in Fast PCR of *Salmonella* in the presence of serum.
Figure 5B:
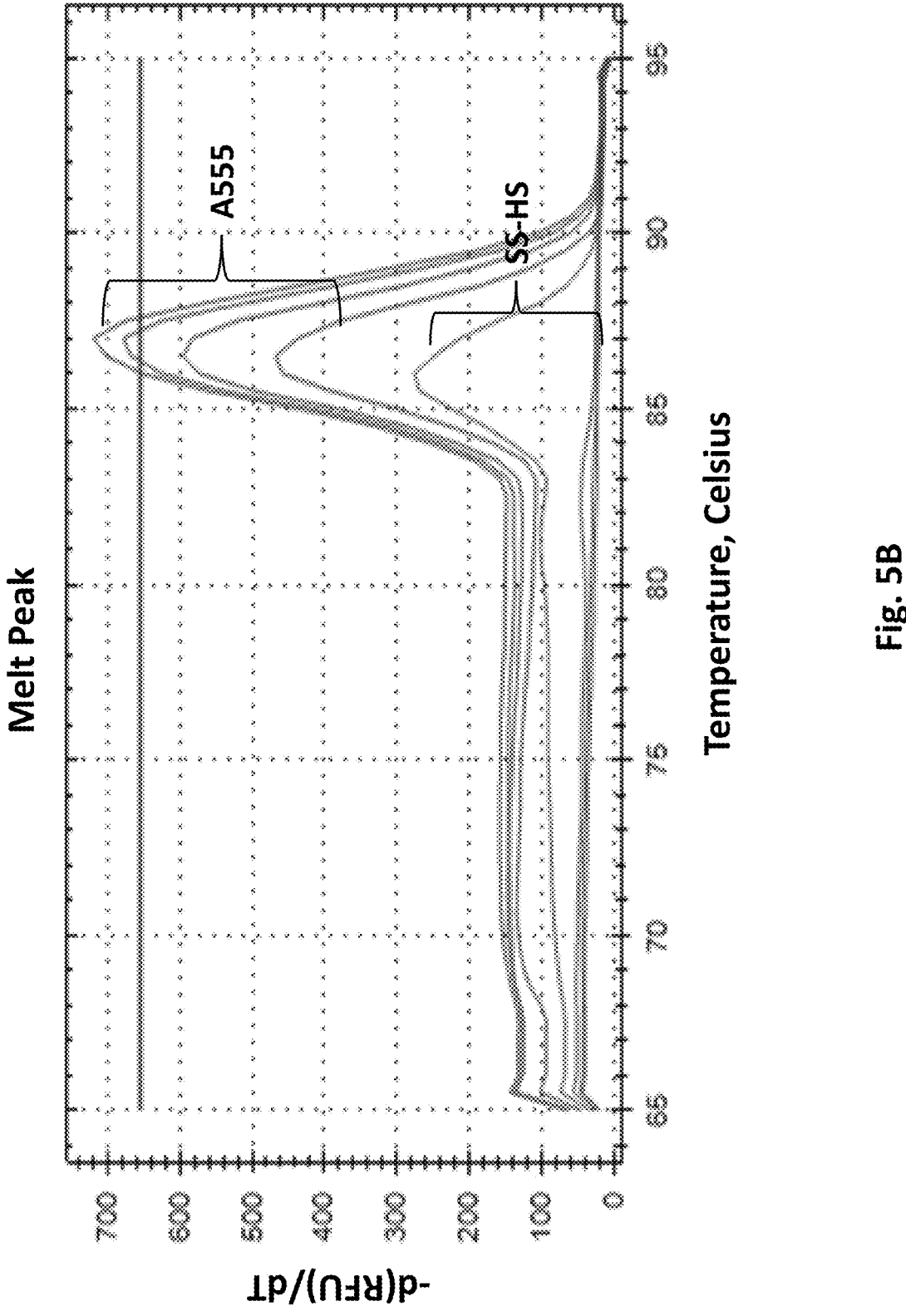
Figure 5C:
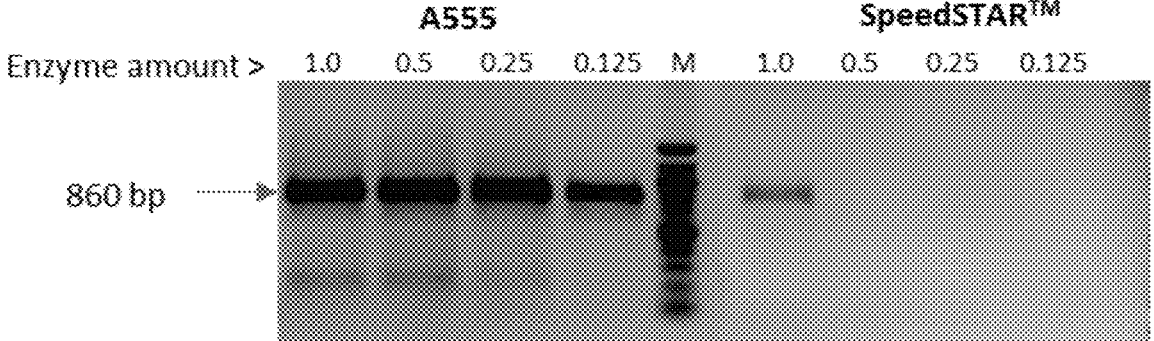

FIG. 5A shows amplification, FIG. 5B shows the melt peak, and FIG. 5C shows an agarose gel. An 860 bp target of *Salmonella* was amplified in real-time PCR with the Taq mutant enzyme A555 from serum spiked with *Salmonella* DNA. A commercial high speed Taq DNA polymerase (SpeedSTAR™ HS) (SS-HS) from Takara was included as comparison. Four 2-fold serial enzyme dilutions were used, starting with 1 ul enzyme/25 ul reaction. Each reaction contained 10% serum, 0.25×SYBR Green, 10 ng DNA. The PCR was performed with an initial denaturation step at 95 deg. for 2 min, followed by 45 cycles of 95 deg/3 sec and 60 deg/1 sec. The amplification and melting curves are show in FIG. 5A and FIG. 5B, respectively. The final PCR products were resolved in an ethidium bromide stained 1.5% agarose gel (FIG. 5C), along with a DNA ladder (lane M). In this fast PCR cycling conditions and presence of human serum, a potent PCR inhibitor, the Taq mutant A555 was able to amplify the target with all enzyme concentrations tested. The commercial SpeedSTAR™ HS enzyme could only amplify this target at the highest concentration, with much delayed CT values.

Figure 6A:
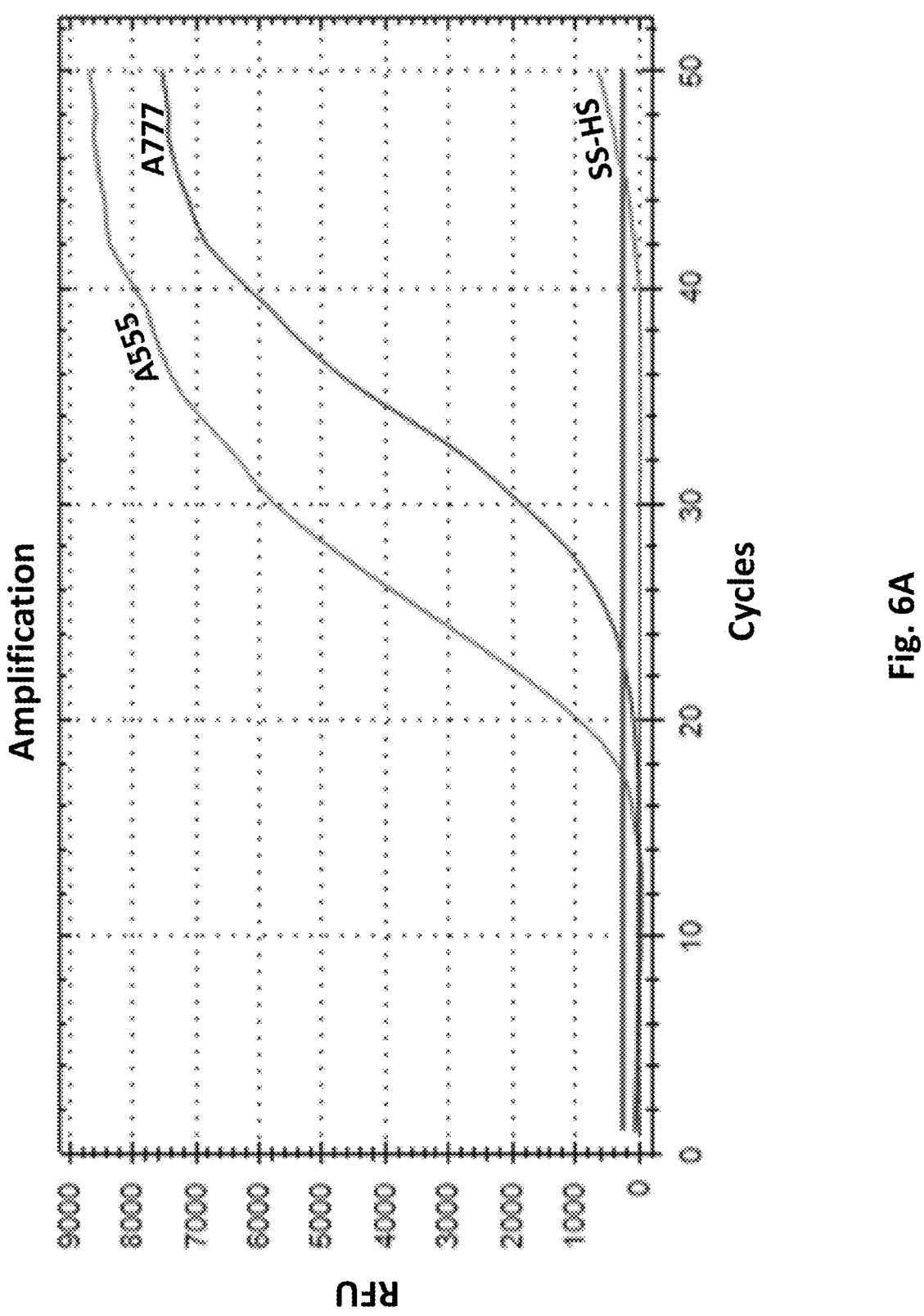
Figure 6B:
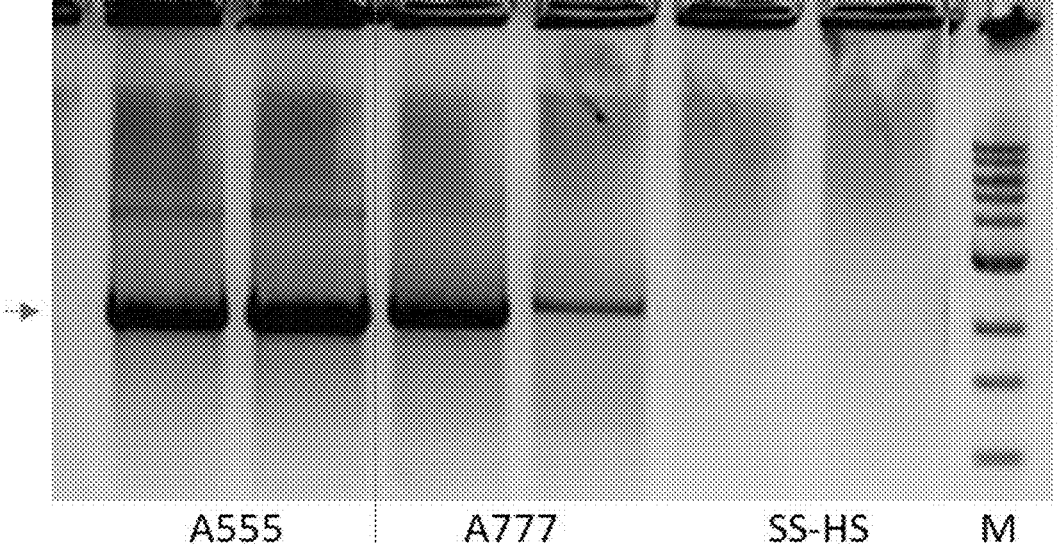

FIGS. 6A and 6B show fast PCR in the presence of human blood for the A555 and A777 Taq mutants vs. SpeedSTAR™ HS polymerase. A 1.8 kb target from the pUC18 plasmid was amplified in real-time PCR in the presence of SYBR Green, with equivalent amounts of the mutant enzymes A555, A777, and SpeedSTAR™ HS (SS-HS) (4 two-fold dilutions each enzyme), in the presence of 5% human blood. The amplification curves, representing the reactions with the highest amounts of each enzyme are shown in FIG. 6A, and an agarose gel image is shown in FIG. 6B. Reactions contained 100 pg plasmid DNA and 15×SYBR Green (such a high concentration of the dye is needed to compensate for the fluorescence quenching effect of the hemoglobin), and the PCR was performed in the reaction buffer recommended for the SpeedSTAR™ HS (SS-HS) enzyme. All reactions contained 0.5×PEC-1 PCR enhancer. Two-step cycling was performed with a 10 sec/94 deg. denaturing step, followed by a 5 sec./62 deg. annealing/extension step, for 50 cycles. The PCR products of the reactions with the two highest amounts of each enzyme were resolved in a 1.5% ethidium bromide stained agarose gel, along with a DNA ladder (lane M). The specific PCR products are pointed by an arrow. The two fast Taq mutants outperformed the commercial SpeedSTAR™ HS fast enzyme, and efficiently amplified this 1.8 kb long target with only 5 sec extension time in the presence of blood, demonstrating their resistance to the known PCR inhibition by blood. The SpeedSTAR™ HS polymerase failed to amplify the target.

Figure 7A:
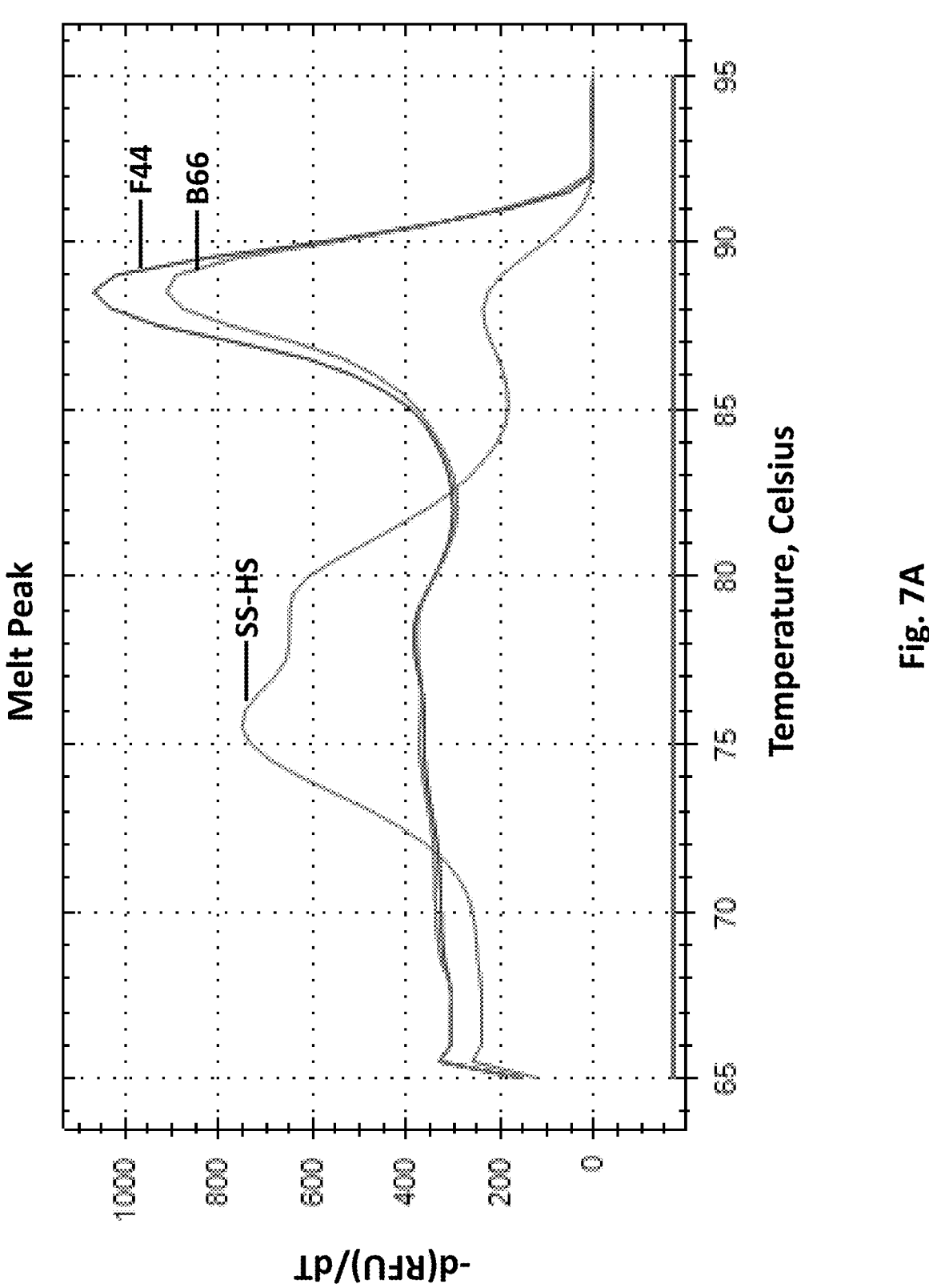
Figure 7B:
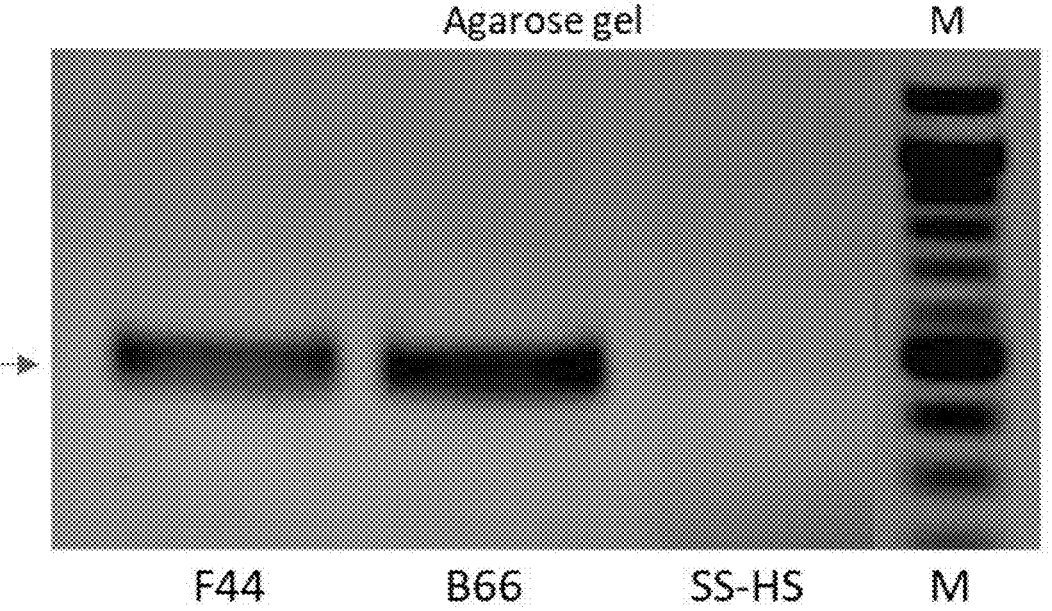

FIGS. 7A and 7B show fast RT-PCR with two reverse transcriptase (RT)-competent Taq mutants, F44 and B66. A 500 nt target of the MS2 phage RNA was amplified in real-time RT-PCR with equivalent amounts of the Taq mutants F44 and B66, or the commercial SpeedSTAR™ HS (SS-HS) polymerase. The melting curves and an agarose gel image are shown in FIG. 7A and FIG. 7B, respectively. The cycling conditions include a reverse-transcriptase step at 68 deg for 30 min, followed by 94 deg/10 sec and 62 deg/1 sec, for 48 cycles. The PCR products were resolved in an ethidium bromide stained 1.5% agarose gel, along with a DNA ladder (M). The specific 500 bp PCR products are pointed by an arrow. The two Taq mutants demonstrated both reverse-transcriptase activity and high speed, which allowed them to efficiently amplify this RNA target with an extension time of only 1 sec. The SpeedSTAR™ HS (SS-HS) enzyme failed to generate specific products in this double challenge PCR test.

Figure 8A:
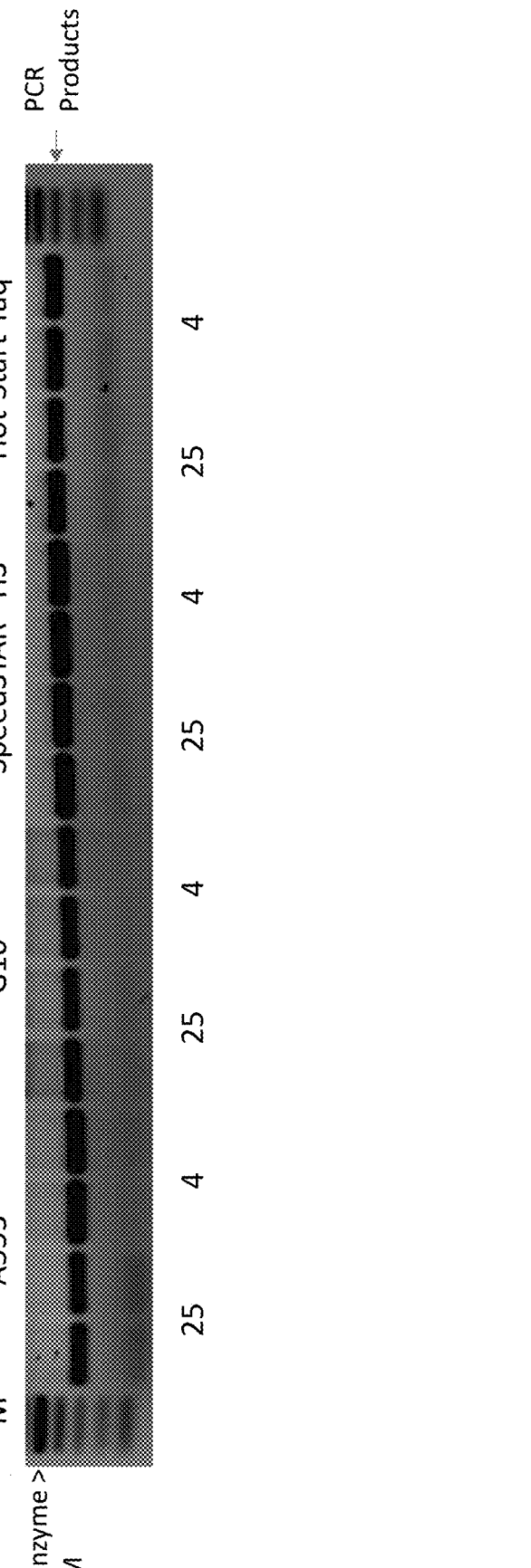
Figure 8B:
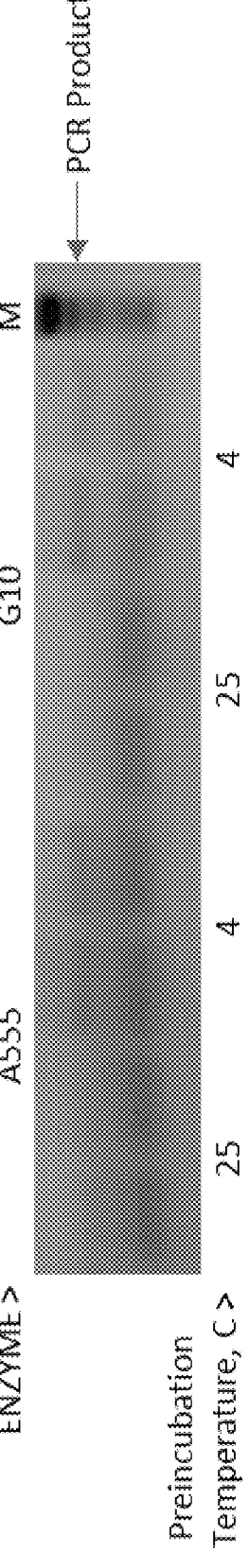

FIGS. 8A and 8B show hot-start PCR performance of the novel fast Taq mutant enzymes. A 320 bp human genomic target was amplified with the Taq mutant enzymes A555 and G10 with (FIG. 8A) or without (FIG. 8B) being complexed with an anti-Taq antibody. Two commercial enzymes, SpeedSTAR™ HS (Takara Bio USA, Irvine, CA) and Hot Start Taq DNA polymerase (New England Biolabs, Beverly, MA) were included as comparison. Specially designed primers and cycling conditions that challenge the specificity of PCR and make it hot-start demanding were used. Four reactions were performed with each enzyme, including a pre-incubation step at 25 deg. or 4 deg. for 1 hour (in duplicates) prior to PCR cycling. This challenging step, when done at 25 deg., allows for formation of non-specific/ primer: dimer products. Without the use of antibody, the A555 and G10 mutant enzymes could only generate weak specific bands in the reactions pre-incubated at 4 deg., but failed in the reactions pre-incubated at 25 deg. Including the anti-Taq antibody, however, allows the two enzymes to amplify this target as specifically and efficiently as the commercial hot-start enzymes (no matter if the reactions were pre-incubated at 25 deg. or 4 deg.) This demonstrates that the novel fast Taq mutants can be easily rendered hot-start performing with the well-established antibody complexation protocol.

DETAILED DESCRIPTION

Definitions

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "include," "includes," and "including" are to be construed as at least having the features to which they refer while not excluding any additional unspecified features.

The phrase "operably linked" as used herein refers to the joining of nucleic acid or amino acid sequences such that one sequence can provide a function to a linked sequence. In the context of a promoter, "operably linked" means that the promoter is connected to a sequence of interest such that the transcription of that sequence of interest is controlled and regulated by that promoter. When the sequence of interest encodes a protein that is to be expressed, "operably linked" means that the promoter is linked to the sequence in such a way that the resulting transcript will be efficiently translated. If the linkage of the promoter to the coding sequence is a transcriptional fusion that is to be expressed, the linkage is made so that the first translational initiation codon in the resulting transcript is the initiation codon of the coding sequence. Alternatively, if the linkage of the promoter to the coding sequence is a translational fusion and the encoded protein is to be expressed, the linkage is made so that the first translational initiation codon contained in the 5' untranslated sequence associated with the promoter and the coding sequence is linked such that the resulting translation product is in frame with the translational open reading frame that encodes the protein.

Where a term is provided in the singular, other embodiments described by the plural of that term are also provided.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Further Description

The present disclosure provides new *Thermus aquaticus* (Taq) and Klentaq DNA polymerase mutants that exhibit fast DNA polymerase elongation rate activity, hereinafter collectively referred to as "fast Taq mutants." In certain embodiments, fast Taq mutants include polypeptides set forth in SEQ ID NO: 3-8, 12-18, and variants thereof. In certain embodiments, the fast Taq mutants can also tolerate high levels of major PCR inhibitors. In certain embodiments, the fast Taq mutants can also be used in conjunction with agents which provide for "hot start" PCR reactions (e.g., anti-Taq antibodies, anti-Taq monoclonal antibodies, and/or anti-Taq aptamers). In certain embodiments, such fast Taq mutants can be used in polymerase chain reactions (PCRs) with short primer extension steps (e.g., about 0.5 seconds or 1 second to about 4 seconds or 5 seconds) to produce PCR amplification products that include amplicons of at least 0.5 kBp, 1 kBp, 2 kBp, or more base pairs in length. In certain embodiments, PCR amplification products of about 0.5 kBp or 1 kBp to about 2 kBp, 4 kBp, 5 kBp, or more are produced in polymerase chain reactions (PCRs) with short primer extension steps (e.g., about 0.5 seconds or 1 second to about 4 seconds or 5 seconds) using fast Taq mutants provided herein (e.g. SEQ ID NO: 3-8, 12-18, and variants thereof).

In certain embodiments, certain mutant polymerases provided herein, including SEQ ID NO: 6, 7, 8, and variants thereof, can have fast DNA polymerase elongation rate activity, reverse transcriptase activity, and/or strand displacement activity. Methods of amplifying a target nucleic acid using mutant polymerases having DNA polymerase activity, reverse transcriptase activity, and/or strand displacement activity are provided herein. In some embodiments of the methods, amplifying comprises reverse transcriptase PCR (RT-PCR). In some embodiments, amplifying comprises loop-mediated isothermal amplification (LAMP). In some embodiments, LAMP is performed with a hanging drop hot start. In some embodiments, amplifying comprises reverse transcriptase loop-mediated isothermal amplification (RT-LAMP). In some embodiments, RT-LAMP is performed with a hanging drop hot start. In certain embodiments, mutant polymerases provided herein, including SEQ ID NO: 6, 7, 8, and variants thereof, are used in an RT-PCR or RT-LAMP assay mixture which does not include a separate reverse transcription enzyme and/or Mn$^{++}$ ion. Methods for using RT-PCR or RT-LAMP assay mixtures, including such assay mixtures which do not include a separate reverse transcription enzyme and/or Mn$^{++}$ ion, can be adapted for use with the mutant polymerases provided herein from the disclosure of U.S. Pat. No. 11,091,745, which is incorporated herein in its entirety with respect to such disclosure.

Except as otherwise noted herein, the fast Taq mutants can be used in PCR amplification methods adapted from those set forth in the following U.S. patents, U.S. patent applications and International Patent Application publications, which are each incorporated herein by reference in their entirety: U.S. Pat. No. 7,462,475, issued 9 Dec. 2008; U.S. Pat. No. 10,683,537, issued Jun. 16, 2020; U.S. Pat. No. 11,091,745, issued Aug. 17, 2021; U.S. Patent Application Publication No. 2009/0170060, published 2 Jul. 2009; U.S. Patent Application Publication No. 2011/0027832, published 3 Feb. 2011; U.S. Patent Application Publication No. 201210028259, published 2 Feb. 2012; U.S. Patent Application Publication No. 2013/0040365, published 14 Feb. 2013; and international PCT application WO20121088479, published 28 Jun. 2012. One adaptation of the PCR amplification methods set forth in the aforementioned U.S. patents, U.S. patent applications and International Patent Application publications that can be implemented with the new Taq and Klentaq DNA polymerase mutants that exhibit fast DNA polymerase elongation rate activity is the use of shorter primer extension steps in the PCR reactions (e.g., 0.5 seconds or 1 second to about 2 seconds, 3 seconds, 4 seconds, or 5 seconds). With the fast Taq mutants provided herein, such shorter primer extension steps can be used even with PCR reactions which produce amplicons of at least 0.5 kBp, 1 kBp, 2 kBp, or more base pairs in length or which produce amplicons of about 0.5 kBp or 1 kBp to about 2 kBp, 4 kBp, 5 kBp, or more in length.

According to conventional notation, amino acid mutations discussed herein may be represented, from left to right, by the one letter code for the wild type amino acid, the amino acid position number, and the one letter code for the mutant amino acid. For mutant polypeptide sequences, an amino acid different than corresponding wild type may be represented, from left to right, by the amino acid position number and the one letter code for the amino acid that is different than corresponding wild type.

For the following discussion, wild type Taq numbering (corresponding to numbering of full-length Taq of SEQ ID NO: 1) is used in this descriptive text so as to make clear the relationship between the polypeptides. Wild type Taq (SEQ ID NO: 1) and truncated Klentaq-1 (SEQ ID NO: 2) have complete sequence homology across positions 279-832 of SEQ ID NO: 1, except for positions 279 (Gly) and 280 (Ser) of SEQ ID NO: 1 (corresponding to positions 1 (Met) and 2 (Gly) of truncated SEQ ID NO: 2). The amino acid changes at 279-280 of wild type Taq (SEQ ID NO: 1) and positions 1-2 of truncated Klentaq-1 (SEQ ID NO: 2) are not necessarily associated with a difference in phenotype as described herein.

With respect to wild-type Taq numbering, for truncated polymerase polypeptides (e.g., Klentaq-1 of SEQ ID NO: 2), position number 1 as notated in the Sequence Listing of SEQ ID NO: 2 corresponds to position number 279 as notated in the full-length wild-type Taq DNA polymerase of SEQ ID NO: 1. Similarly, position number 2 of SEQ ID NO: 2 corresponds to position number 280 of SEQ ID NO: 1. Similarly, position number 554 of SEQ ID NO: 2 corresponds to position number 832 of SEQ ID NO: 1. In other words, one can determine the corresponding position in full-length SEQ ID NO:1 by adding 278 the any position in SEQ ID NO: 2.

Fast Taq polymerase mutants provided herein include DNA polymerases comprising a polypeptide sequence having at least 95% sequence identity to positions 279 through 832 of SEQ ID NO: 1, and further comprising one or more amino acid substitution selected from the group consisting of A391T, P752S, A814T, and combinations thereof, wherein all amino acid substitutions are relative to SEQ ID NO: 1. In certain embodiments, the aforementioned Taq polymerase mutants can further comprise further one or more amino acid substitutions selected from the group consisting of D732N, D732R, D732K, K738R, E742R, E742K, A743R, A743K, E818V, and combinations thereof, wherein all amino acid substitutions are relative to SEQ ID NO: 1. Wild-type Taq DNA polymerase, Klentaq, non-limiting examples of fast Taq mutants provided herein, and sequences which contain one or more mutations found in fast Taq mutants include those set forth in Table 1 and provided in the accompanying sequence listing.

TABLE 1

Wild-type Taq, Klentaq, and mutant Taq polymerase sequence descriptions.

| Description of Sequence | SEQ ID NO | Type of Sequence | Organism |
|---|---|---|---|
| WT TAQ FULL LENGTH (832 aa) | 1 | PRT | *Thermus aquaticus* |
| KLENTAQ (554 aa) | 2 | PRT | Artificial |
| A555 (Full length 832 aa Taq mutant comprising A391T, D732N, E742R, A743R, P752S, and E818V amino acid substitutions relative to SEQ ID NO: 1) | 3 | PRT | Artificial |
| A777 (Full length 832 aa Taq mutant comprising D732K, E742K, and A743R amino acid substitutions relative to SEQ ID NO: 1) | 4 | PRT | Artificial |
| G10 (Full length 832 aa Taq mutant comprising D732N, E742R, A743R, P752S, and E818V amino acid substitutions relative to SEQ ID NO: 1) | 5 | PRT | Artificial |
| F40 (Full length 832 aa Taq mutant comprising D732N, K738R, E742R, and A743R amino acid substitutions relative to SEQ ID NO: 1) | 6 | PRT | Artificial |
| F44 (Full length 832 aa Taq mutant comprising D732N, E742R, A743R, and A814T amino acid substitutions relative to SEQ ID NO: 1) | 7 | PRT | Artificial |
| B66 (Full length 832 aa Taq mutant comprising D732N, E742R, A743R, and E818V amino acid substitutions relative to SEQ ID NO: 1) | 8 | PRT | Artificial |
| A391T (Full length 832 aa Taq mutant comprising the A391T amino acid substitution relative to SEQ ID NO: 1) | 9 | PRT | Artificial |
| P752S (Full length 832 aa Taq mutant comprising the P752S amino acid substitution relative to SEQ ID NO: 1) | 10 | PRT | Artificial |
| A814T (Full length 832 aa Taq mutant comprising the A814T amino acid substitution relative to SEQ ID NO: 1) | 11 | PRT | Artificial |
| A555 KLENTAQ (554 aa KLENTAQ mutant comprising A391T, D732N, E742R, A743R, P752S, and E818V amino acid substitutions relative to SEQ ID NO: 1) | 12 | PRT | Artificial |
| A777 KLENTAQ (554 aa KLENTAQ mutant comprising D732K, E742K, and A743R amino acid substitutions relative to SEQ ID NO: 1) | 13 | PRT | Artificial |
| G10 KLENTAQ (554 aa KLENTAQ mutant comprising D732N, E742R, A743R, P752S, and E818V amino acid substitutions relative to SEQ ID NO: 1) | 14 | PRT | Artificial |

TABLE 1-continued

Wild-type Taq, Klentaq, and mutant Taq polymerase sequence descriptions.

| Description of Sequence | SEQ ID NO | Type of Sequence | Organism |
|---|---|---|---|
| F40 KLENTAQ (554 aa KLENTAQ mutant comprising D732N, K738R, E742R, and A743R amino acid substitutions relative to SEQ ID NO: 1) | 15 | PRT | Artificial |
| F44 KLENTAQ (554 aa KLENTAQ mutant comprising D732N, E742R, A743R, and A814T amino acid substitutions relative to SEQ ID NO: 1) | 16 | PRT | Artificial |
| B66 KLENTAQ (554 aa KLENTAQ mutant comprising D732N, E742R, A743R, and E818V amino acid substitutions relative to SEQ ID NO: 1) | 17 | PRT | Artificial |
| A391T KLENTAQ (554 aa KLENTAQ mutant comprising the A391T amino acid substitution relative to SEQ ID NO: 1) | 18 | PRT | Artificial |
| P752S KLENTAQ (554 aa KLENTAQ mutant comprising the P752S amino acid substitution relative to SEQ ID NO: 1) | 19 | PRT | Artificial |
| A814T KLENTAQ (554 aa KLENTAQ mutant comprising the A814T amino acid substitution relative to SEQ ID NO: 1) | 20 | PRT | Artificial |

A fast Taq mutant polymerase having a mutation described herein can be a full length mutant polymerase or a truncated mutant polymerase, as compared to a wild-type Taq polymerase. For example, a truncated mutant polymerase can be truncated at position 278 per wild-type Taq numbering (e.g., position 1 of the truncated mutant corresponds to position 279 of SEQ ID NO: 1). One of skill in the art will understand that a truncated mutant polymerase can be truncated at any position of a full length sequence so long as polymerase activity is retained. Truncated mutant polymerases provided herein include the polypeptides of SEQ ID NO: 12, 13, 14, 15, 16, 17, 18, 19, 20, and variants thereof having at least 95%, 96%, 97%, 98%, or 99% sequence identity to least positions 279 through 832 of SEQ ID NO: 1 or across the entire length of SEQ ID NO: 2.

A truncated mutant polymerase can be referred to as a "functional fragment" of a longer polymerase, such as a full-length polymerase. For example, SEQ ID NO: 2 (Klentaq-1, KT-1) is a variant (having G279M and S280G per wild type Taq numbering) and functional fragment of SEQ ID NO: 1 (wild type Taq). As another example is Omni Kt (KT-10; described in U.S. Patent Application Publication No. 2006/0084074 which is incorporated herein by example in its entirety) is a functional fragment of Omni Taq (FL-22; described in U.S. Patent Application Publication No. 2011/0027832 which is incorporated herein by example in its entirety). A functional fragment is shorter than the length of a reference polymerase and retains polymerase activity. Functional fragments provided herein include of functional fragments of longer polymerases provided herein (e.g., the polypeptides of SEQ ID NO: 3, 4, 5, 6, 7, 8, 9, 10, 11, and variants thereof having at least 95%, 96%, 97%, 98%, or 99% sequence identity to at least positions 279 through 832 of SEQ ID NO: 1 or across the entire length of SEQ ID NO: 1).

One or more amino acid mutations (e.g., addition, deletion, substitution) can be associated with a fast DNA polymerase elongation rate phenotype described herein. Such fast elongation rate phenotypes include elongation rates of about 0.5 or 1 to about 2, 3, 4, or 5 seconds/kilobase. In certain embodiments, a mutant polymerase (e.g., a full length mutant polymerase or a truncated mutant polymerase) having a fast elongation rate phenotype can include one or more of the following substitutions: A391T, P752S, A814T, and combinations thereof, wherein all amino acid substitutions are relative to SEQ ID NO: 1. In certain embodiments, the mutant polymerase comprising the A391T, P752S, and/or A814T substitutions can further comprise one or more D732N, D732R, D732K, K738R, E742R, E742K, A743R, A743K, and/or E818V substitutions, wherein all amino acid substitutions are relative to SEQ ID NO: 1. In certain embodiments, the mutant polymerase having a fast elongation rate phenotype comprises the following combinations of amino acid substitutions relative to SEQ ID NO: 1: (a) A391T; (b) D732N, D732R, or D732K; (c) P752S; (d) E742R or E742K; (e) A743R or A743K; and (0 E818V. In certain embodiments, the mutant polymerase having a fast elongation rate phenotype comprises the following combinations of amino acid substitutions relative to SEQ ID NO: 1: (a) D732N, D732R, or D732K; (b) P752S; (c) E742R or E742K; (d) A743R or A743K; and (e) E818V. In certain embodiments, the mutant polymerase having a fast elongation rate phenotype comprises the following combinations of amino acid substitutions relative to SEQ ID NO: 1: (a) D732N, D732R, or D732K; (b) E742R or E742K; (c) A743R or A743K; and (d) A814T. In certain embodiments, a mutant polymerase (e.g., a full length mutant polymerase or a truncated mutant polymerase) having a fast elongation rate phenotype can include one of the following combinations of amino acid substitutions relative to SEQ ID NO: 1: (i) A391T, D732N, E742R, A743R, P752S, and E818V (e.g., SEQ ID NO: 3 or SEQ ID NO: 12); (ii) D732N, E742R, A743R, P752S, and E818V (e.g., SEQ ID NO: 5 or SEQ ID NO: 14); or (iii) D732N, E742R, A743R, and A814T (e.g., SEQ ID NO: 7 or SEQ ID NO: 16). In certain embodiments, the full length or truncated mutant polymerase comprising any of the aforementioned polypeptides can have at least 95%, 96%, 97%, 98%, or 99% sequence identity to SEQ ID NO: 1 or can have at least 95%, 96%, 97%, 98%, or 99% sequence identity to positions 279 through 832 of SEQ ID NO: 1.

A mutant polymerase described herein can be used in conjunction with compositions or processes described in U.S. Pat. Nos. 6,403,341; 7,393,635; 7,462,475; WO 2012/088479 (and corresponding U.S. application Ser. No. 13/997,194); and U.S. Pat. App. Pub. No. 201210028259, each incorporated herein by reference.

Mutant polymerases provided herein can also be used in conjunction with agents which bind and inactivate the polymerase at ambient temperatures but which can in turn be inactivated by high temperatures for use in hot start PCR reactions. In certain embodiments, such agents can comprise anti-Taq antibodies or anti-Taq monoclonal antibodies, including those which are commercially available (e.g., TaqStart® Antibody, Takara Bio USA, Irvine, CA; Platinum® Taq, Invitrogen, San Diego, CA; JumpStart™ Taq, Sigma, St. Louis, MO, USA), described in non-patent literature (Kellogg et al. (1994) Biotechniques 16:1134-1137), or described in the patent literature (U.S. Pat. App. Pub. No. 2017/0037458 and U.S. Pat. No. 5,338,671, each incorporated by reference in their entireties). In certain embodiments, such agents can comprise anti-Taq aptamers including those which are commercially available (e.g. Hot Start Taq, New England Biolabs, Beverly, MA, USA) or described in the patent literature (U.S. Pat. Nos. 6,020,130 and 6,183,967, each incorporated herein by reference in their entireties). In certain embodiments, the mutant polymerases can be provided in a composition where the polymerase is complexed (e.g., non-covalently bound) to the anti-Taq antibodies, anti-Taq monoclonal antibodies, or anti-Taq aptamers. In certain embodiments, the mutant polymerases can be provided in a kit where the polymerase and the anti-Taq antibodies, anti-Taq monoclonal antibodies, or anti-Taq aptamers are provided in separate containers.

Another aspect of the present disclosure provides a recombinant polynucleotide encoding a mutant polymerase described herein. Also provided is a nucleic acid construct (e.g., an expression vector) including polynucleotide encoding a mutant polymerase described herein. A construct (e.g., a DNA construct) can include the following operably linked components: a heterologous or endogenous promoter functional in a host cell, a nucleotide sequence (e.g., a heterologous DNA sequence, an exogenous DNA segment, or a heterologous nucleic acid) encoding a mutant polymerase described herein, a transcriptional termination sequence.

The term "variant" polypeptides (or encoding polynucleotides) is discussed below. The description of "variant" below is incorporated by reference into each recitation of "variant" in the description of mutant polymerases herein. For example, the full range of sequence identity discussed below applies equally to "variant" polypeptides discussed elsewhere herein. Included in the scope of the present disclosure are variant polypeptides (or encoding polynucleotides) with at least 80% at least about 85%, 86%, 87%, 88%, 89%, 90%, 91%, 92%, 93%, 94%, 95%, 96%, 97%, 98%, 99%, or 99.9% sequence identity to a polypeptide sequence having at least 95% sequence identity to positions 279 through 832 of SEQ ID NO: 1, and further comprising one or more amino acid substitution selected from the group consisting of A391T, P752S, A814T, and combinations thereof, or optionally further comprising one or more amino acid substitutions selected from the group consisting of D732N, D732R, D732K, K738R, E742R, E742K, A743R, A743K, E818V, and combinations thereof, wherein all amino acid substitutions are relative to SEQ ID NO: 1. Included in the scope of the present disclosure are variant polypeptides (or encoding polynucleotides) with at least 80% at least about 85%, 86%, 87%, 88%, 89%, 90%, 91%, 92%, 93%, 94%, 95%, 96%, 97%, 98%, 99%, or 99.9% sequence identity to sequences disclosed herein, including disclosed sequences having substitutions described herein such as SEQ ID NO: 3, 4, 5, 6, 7, 8, 9, 10, 11, 12, 13, 14, 15, 16, 17, 18, 19, or 20), so long as such variants retain a polymerase activity (e.g., a fast elongation rate phenotype and/or a PCR-inhibitor resistant polymerase activity). In certain embodiments, a variant polypeptide (or an encoding polynucleotide) with polymerase activity can have at least about 85%, 86%, 87%, 88%, 89%, 90%, 91%, 92%, 93%, 94%, 95%, 96%, 97%, 98%, 99%, or 99.9% sequence identity to sequences disclosed herein (including disclosed sequences having substitutions described herein such as SEQ ID NO: 3, 4, 5, 6, 7, 8, 9, 10, 11, 12, 13, 14, 15, 16, 17, 18, 19, or 20). It is understood that in some embodiments "about" modifies each of these recited sequence identity values. A variant polypeptide (or encoding polynucleotides) with polymerase activity can have at least 95% sequence identity to a sequence disclosed herein. A variant polypeptide (or an encoding polynucleotide) with polymerase activity can have at least 99% sequence identity to a sequence disclosed herein. The species are representative of the genus of variant polypeptides of each of these respective sequences because all variants must possess the specified catalytic activity (e.g., resistant polymerase activity) and must have the percent identity required above to the reference sequence. Design, generation, and testing of the variant polypeptides having the above required percent identities to the sequences of the mutant DNA polymerases and retaining a fast elongation rate phenotype can be achieved based on the disclosure provided herein. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. In certain embodiments, conservative amino acid substitutions can be made residues of mutant polymerases set forth in SEQ ID NO: 3-20 to obtain variants thereof. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (anionic; negatively charged) amino acids such as aspartic acid and glutamic acid; (2) basic (cationic; positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine. Conservative amino acid changes within mutant polymerase variant sequences (e.g., variants of SEQ ID NO: 3-20) can be made by substituting one amino acid within one of these groups with another amino acid within the same group. In certain embodiments, variants of mutant polymerases set forth in SEQ ID NO: 3-20 will comprise amino acid substitutions selected from the group consisting of A391T, P752S, A814T, D732N, D732R, D732K, K738R, E742R, E742K, A743R, A743K, E818V, and combinations thereof and additional conservative substitutions of other amino acid residues in SEQ ID NO: 3-20.

Amino acid sequence identity percent (%) is understood as the percentage of amino acid residues that are identical with amino acid residues in a candidate sequence in comparison to a reference sequence when the two sequences are aligned. To determine percent amino acid identity, sequences are aligned and if necessary, gaps are introduced to achieve the maximum percent sequence identity; conservative substitutions are not considered as part of the sequence identity. Amino acid sequence alignment procedures to determine percent identity are well known to those of skill in the art. Often publicly available computer software, such as BLAST, BLAST2, ALIGN2 or Megalign (DNASTAR) software, is used to align peptide sequences. Those skilled in the art can determine appropriate parameters for measuring alignment, including any algorithms needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=X/Y100, where X is the number of amino acid residues scored as identical matches by the sequence alignment program's or algorithm's alignment of A and B, and Y is the total number of amino acid residues in B. If the length of amino acid sequence A is not equal to the length of amino acid sequence B, the percent amino acid sequence identity of A to B will not equal the percent amino acid sequence identity of B to A.

A mutant polymerase (including all variants thereof) described herein can be used in a variety of polymerase reactions known to the art (see e.g., Dorak (2006) Real-Time PCR, Taylor & Francis, ISBN 041537734X; Bustin, ed. (2004) A-Z of Quantitative PCR, International University Line, ISBN 0963681788; King and O'Connel (2002) RT-PCR Protocols, 1.sup.st Ed., Human Press, ISBN-10 0896038750). For example, a mutant polymerase can be employed in PCR reactions, primer extension reactions, etc. For example, a mutant polymerases described herein can be used in nucleic acid amplification processes (either alone or in combination with one or more other enzymes), such as Allele-specific PCR; Assembly PCR or Polymerase Cycling Assembly; Asymmetric PCR; Linear-After-The-Exponential-PCR; Helicase-dependent amplification; Hot-start PCR; Intersequence-specific PCR; Inverse PCR; Ligation-mediated PCR; Methylation-specific PCR; Miniprimer PCR; Multiplex Ligation-dependent Probe Amplification; Multiplex-PCR; Nested PCR; Overlap-extension PCR; Quantitative PCR; Quantitative End-Point PCR; Quantitative Real-Time PCR; RT-PCR (Reverse Transcription PCR); Solid Phase PCR; Thermal asymmetric interlaced PCR; Touchdown PCR; PAN-AC; Universal Fast Walking; Long PCR; Rapid Amplified Polymorphic DNA Analysis; Rapid Amplification of cDNA Ends (RACE); Differential Display PCR; In situ PCR; High-Fidelity PCR; PCR or DNA Sequencing (cycle sequencing).

A target nucleic acid of a sample can be any target nucleic acid of interest. For example, a target nucleic add can be a deoxyribonucleic acid (DNA), a ribonucleic acid (RNA), or an artificial nucleic add analog (e.g., a peptide nucleic acid, morpholino- and locked nucleic acid, glycol nucleic acid, or threose nucleic add).

A primer is understood to refer to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

A target nucleic acid, e.g., a template DNA molecule, is understood to be a strand of a nucleic acid from which a complementary nucleic acid strand can be synthesized by a DNA polymerase, for example, in a primer extension reaction.

In some embodiments, the use of a mutant polymerase enzyme described herein does not require substantial changes in the typical protocol but can, for example, allow for the desired use of shorter primer extension times and/or for the presence of higher concentrations of inhibitory substances. A mutant polymerase described herein, and methods for use thereof, can allow for elimination or substantial elimination of an enrichment step for sample preparation. Eliminating an enrichment step can significantly reduce the time to detection or quantification.

A mutant polymerase described herein can be used in an end-point PCR. For example, end-point PCR is commonly carried out in a reaction volume of about 10-200mu·1 in small reaction tubes (about 0.2-0.5 ml volumes) in a thermal cycler. A mutant polymerase described herein can be used with a variety of commercially available end-point PCR kits. The use of a mutant polymerase enzyme described herein generally does not require substantial changes in the typical end-point PCR protocol, but can allow, for example, for the desired use of shorter primer extension times and/or a sample having a higher amount of an inhibitory substance.

A mutant polymerase described herein can be used in real-time PCR (also known as a quantitative polymerase chain reaction (qPCR)). For example, a mutant polymerase described herein can be used in a real-time PCR assay featuring a non-specific fluorescent dye (e.g., a fluorochrome) that can intercalate with any double-stranded DNA. With a non-specific fluorescent dye, an increase in DNA product during PCR can lead to an increase in fluorescence intensity and is measured at each cycle, thus allowing DNA concentrations to be quantified.

As another example, a mutant polymerase described herein can be used in a real-time PCR assay featuring a hybridization probe. As another example, a mutant polymerase described herein can be used in a real-time PCR multiplex assay featuring a hybridization probe. A hybridization probe can be a sequence-specific DNA probe including a fluorescent reporter at one end and a quencher of fluorescence at the opposite end of the probe, where break down of the probe by a 5' to 3' exonuclease activity of a polymerase can break the reporter-quencher proximity and thus allow unquenched emission of fluorescence, which can be detected after excitation with a laser (e.g., a TaqMan® assay). With a hybridization probe, an increase in the product targeted by the reporter probe at each PCR cycle can cause a proportional increase in fluorescence due to the breakdown of the probe and release of the reporter. A mutant polymerase described herein can be used with a variety of commercially available real-time PCR kits.

Thus, methods described herein can be applied to improve the nucleic acid detection in an end-point PCR or a real-time PCR.

In some embodiments, a mutant polymerase described herein can be used in combination with an enzyme having reverse transcriptase activity in a real-time reverse transcriptase (RT) PCR amplification of an RNA target. It is noted that reverse transcriptase (RT) PCR is not to be confused with real-time polymerase chain reaction (Q-PCR), which is sometimes (incorrectly) abbreviated as RT-PCR in the art. In RT-PCR, an RNA strand is first reverse transcribed into its DNA complement (complementary DNA, or cDNA) using the enzyme reverse transcriptase, and the resulting cDNA is amplified using traditional PCR. Like with end-point PCR, conventional RT-PCR protocols require extensive purification steps prior to amplification to purify RNA from inhibitors and ribonucleases, which can destroy the RNA template. Both the inhibition and degradation of RNA are major concerns in important clinical and diagnostics tests, which may lead to false-negative results.

The buffer for use in the various PCR assay mixtures described herein is generally a physiologically compatible buffer that is compatible with the function of enzyme activities and enables cells or biological macromolecules to retain their normal physiological and biochemical functions. Typically, a physiologically compatible buffer will include a buffering agent (e.g., TRIS, MES, PO.sub.4, HEPES, etc.), a chelating agent (e.g., EDTA, EGTA, or the like), a salt (e.g., ammonium sulfate, NaCl, KCl, MgCl$_2$, CaCl$_2$, NaOAc, KOAc, Mg(OAc)$_2$, etc.) and optionally a stabilizing agent (e.g., sucrose, glycerine, Tween20, etc.).

Various PCR additives and enhancers can be employed with the methods described herein. For example, betaine (e.g., MasterAmp™ 10.times. PCR, Epicentre Biotechnologies) can be added to the PCR assay, to further aid in overcoming the inhibition by inhibitory substances described herein. Betaine can be included at final concentration about 1 M to about 2M. Generally, betaine alone is insufficient to overcome the inhibition of various inhibitory substances described herein when used with conventional DNA polymerases.

As another example, a mutant polymerase described herein can be used in conjunction with a PCR enhancer described in U.S. Pat. Pub. No. 2012/0028259 or WO 2012/088479, each incorporated herein by reference. For example, a mutant polymerase can be used in conjunction with a PCR enhancer including trehalose (e.g., about 0.1 to about 1.0 M D-(+)-trehalose per amplification reaction mixture volume), carnitine (about 0.1 to about 1.5 M L-carnitine per amplification reaction mixture volume), or a non-ionic detergent (e.g., Brij-58, NP-40, Nonidet P-40, Igepal CA-630, Brij-58, Tween-20, NP-40, or Triton X-100 at about 0.01% to about 8% non-ionic detergent per amplification reaction mixture volume) or optionally one or more of heparin (e.g., an amount of heparin equivalent to about 2 units to about 50 units heparin per mL of whole blood, plasma, or serum in an amplification reaction mixture), casein (at least about 0.05% up to about 2.5% per amplification reaction mixture volume), or polyvinylpyrrolidone (PVP) or a modified polymer of PVP (PVPP) (e.g., about 0.1% up to about 25%). As another example, a mutant polymerase can be used in conjunction with a PCR enhancer including about 0.6 M trehalose per amplification reaction mixture volume; about 0.5 M carnitine per amplification reaction mixture volume; or a non-ionic detergent (e.g., a polyoxyethylene cetyl ether at about 0.04% to about 0.2% or a nonyl phenoxylpolyethoxylethenol at about 0.4% to about 0.8% per amplification reaction mixture volume); or optional heparin at about 10 units per mL of whole blood, blood fraction, plasma, or serum.

As another example, a mutant polymerase described herein can be used in conjunction with commercially available PCR amplification reaction enhancers, such as MasterAmp™10.times. PCR Enhancer, Epicentre Biotechnologies; TaqMaster PCR Enhancer, MasterTaq Kit, PCR Extender System, 5 PRIME GmbH; Hi-Spec Additive, Bioline; PCRboost™, Biomatrica™; PCRX Enhancer System.

Invitrogen; Taq Extender™ PCR Additive, Perfect Match™ PCR Enhancer, Stratagene; Polymer-Aide PCR Enhancer, Sigma-Aldrich.

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a mutant polymerase described herein or a nucleic acid encoding such mutant polymerase or, optionally, a primer, a buffer, or other composition or component (e.g., a magnesium salt, an anti-Taq antibody, anti-Taq monoclonal antibody, or anti-Taq aptamer) necessary or helpful for PCR. In certain embodiments, the mutant polymerase can be complexed (e.g., non-covalently bound) to an anti-Taq antibody, anti-Taq monoclonal antibody, or anti-Taq aptamer in a composition provided in the kit. In certain embodiments, the mutant polymerase and an anti-Taq antibody, anti-Taq monoclonal antibody, or anti-Taq aptamer are provided separately in the kit. Such packaging of the components separately can, if desired, be presented in a pack or dispenser device which may contain one or more assay unit forms containing a composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like. In certain embodiments, kits can be supplied with instructional materials. Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Embodiments of the disclosure include the following items.

1. A DNA polymerase comprising: (i) a polypeptide sequence having at least 95% sequence identity to positions 279 through 832 of SEQ ID NO: 1, and further comprising one or more amino acid substitution selected from the group consisting of A391T, P752S, A814T, and combinations thereof, wherein all amino acid substitutions are relative to SEQ ID NO: 1; or (ii)

a polypeptide sequence of any one of SEQ ID NO: 3, 4, 5, 6, 7, 8, 9, 10, 11, 12, 13, 14, 15, 16, 17, 18, 19, 20, or a variant thereof.

2. The DNA polymerase of embodiment 1, wherein said polymerase further comprises one or more amino acid substitutions selected from the group consisting of D732N, D732R, D732K, K738R, E742R, E742K, A743R, A743K, E818V, and combinations thereof, wherein all amino acid substitutions are relative to SEQ ID NO: 1.

3. The DNA polymerase of embodiment 2, wherein said polymerase comprises amino acid substitutions: (a) A391T; (b) D732N, D732R, or D732K; (c) P752S; (d) E742R or E742K; (e) A743R or A743K; and (0 E818V, wherein all amino acid substitutions are relative to SEQ ID NO: 1.

4. The DNA polymerase of embodiment 3, wherein said polymerase comprises amino acid substitutions: (a) A391T; (b) D732N; (c) P752S; (d) E742R; (e) A743R; and (0 E818V, wherein all amino acid substitutions are relative to SEQ ID NO: 1; optionally wherein said polymerase comprises the polypeptide sequence of SEQ ID NO: 3, SEQ ID NO: 12, or a variant thereof 5. The DNA polymerase of embodiment 2, wherein said polymerase comprises amino acid substitutions: (a) D732N, D732R, or D732K; (b) P752S; (c) E742R or E742K; (d) A743R or A743K; and (e) E818V, wherein all amino acid substitutions are relative to SEQ ID NO: 1.

6. The DNA polymerase of embodiment 5, wherein said polymerase comprises amino acid substitutions: (a) D732N; (b) P752S; (c) E742R; (d) A743R; and (e) E818V, wherein all amino acid substitutions are relative to SEQ ID NO: 1; optionally wherein said polymerase comprises the polypeptide sequence of SEQ ID NO: 5, SEQ ID NO: 14, or a variant thereof 7. The DNA polymerase of embodiment 2, wherein said polymerase comprises amino acid substitutions: (a) D732N, D732R, or D732K; (b) E742R or E742K; (c) A743R or A743K; and (d) A814T, wherein all amino acid substitutions are relative to SEQ ID NO: 1.

8. The DNA polymerase of embodiment 7, wherein said polymerase comprises amino acid substitutions: (a) D732N; (b) E742R; (c) A743R; and (d) A814T, wherein all amino acid substitutions are relative to SEQ ID NO: 1; optionally wherein said polymerase comprises the polypeptide sequence of SEQ ID NO:7, SEQ ID NO: 16, or a variant thereof 9. The DNA polymerase of embodiment 1, wherein the DNA polymerase comprises the amino acid substitution of A391T, wherein said amino acid substitution is relative to SEQ ID NO: 1.

10. The DNA polymerase of embodiment 1, wherein the DNA polymerase comprises the amino acid substitution P752S, wherein said amino acid substitution is relative to SEQ ID NO: 1.

11. The DNA polymerase of embodiment 1, wherein the DNA polymerase comprises the amino acid substitution A814T, wherein said amino acid substitution is relative to SEQ ID NO: 1.

12. The DNA polymerase of any one of embodiments 1 to 11, wherein said DNA polymerase comprises: (i) a polypeptide sequence having at least 96%, 97%, 98%, or 99% sequence identity to positions 279 through 832 of SEQ ID NO: 1; or (ii) a polypeptide sequence having at least 95%, 96%, 97%, 98%, or 99% sequence identity to positions 1 through 832 of SEQ ID NO: 1.

13. The DNA polymerase of any one of embodiments 1 to 12, wherein said DNA polymerase is isolated and/or does not occur in nature.

14. The DNA polymerase of any one of embodiments 1 to 13, wherein the polypeptide has polymerase activity in the presence of an inhibitory substance in an amount sufficient to cause a wild-type Taq polymerase comprising SEQ ID NO: 1 to fail to amplify a target nucleic acid in a polymerase chain reaction (PCR), optionally wherein the inhibitory substance comprises one or more of chocolate, peanut butter, milk, seafood, meat, egg, plant material, blood, a blood fraction, urine, dye, soil, soil extract, humic acid, guanidinium thiocyanate (GITC), or ethanol.

15. The DNA polymerase of any one of embodiments 1 to 14, wherein the polypeptide exhibits reverse transcriptase activity, optionally wherein the polypeptide comprises the amino acid sequence of SEQ ID NO: 6, 7, 8, 15, 16, 17, or a variant thereof 16. The DNA polymerase of any one of embodiments 1 to 11, where the polypeptide exhibits an elongation rate of about 0.5 or 1 to about 2.5, 3, or 4 or 5 seconds/kilobase.

17. A recombinant DNA molecule comprising a polynucleotide encoding the DNA polymerase of any one of embodiments 1 to 16, optionally wherein a heterologous promoter is operably linked to the polynucleotide.

18. A cell comprising the DNA molecule of embodiment 17.

19. A method of making the DNA polymerase of any one of embodiments 1 to 16 comprising culturing a cell comprising a polynucleotide encoding the DNA polymerase of any one of embodiments 1 to 16 and isolating the DNA polymerase from the cultured cells.

20. A composition comprising the DNA polymerase of any one of embodiments 1 to 16, optionally wherein the composition further comprises at least one of an anti-Taq antibody, an anti-Taq monoclonal antibody, an anti-Taq aptamer, or a buffering agent.

21. A kit comprising the DNA polymerase of any one of embodiments 1 to 16, optionally wherein the kit further comprises at least one of a positive control template nucleic acid, positive control primer oligonucleotides which provide for polymerase chain reaction-mediated amplification of the positive control template, an anti-Taq antibody, and/or an anti-Taq monoclonal antibody, and/or an anti-Taq aptamer.

22. A method of amplifying a target nucleic acid in a polymerase chain reaction (PCR) comprising: forming an assay mixture comprising a sample comprising a target nucleic acid, primers specific for the target nucleic acid, a buffer, and at least one DNA polymerase of any one of embodiments 1 to 16; and amplifying the target nucleic acid in the assay mixture in a PCR to produce an PCR amplification product.

23. The method of embodiment 22, wherein: (i) the extension cycle for the PCR reaction is about 1 or 2 to about 3, 4, or 5 seconds in duration, optionally wherein the PCR amplification product is at least about 0.5 or 1 kilobase pairs (kBp) in length; (ii) the extension cycle for the PCR reaction is at least about 0.5, 1, 2, 3, 4, or 5 seconds in duration, optionally wherein the PCR amplification product is at least about 0.5 or 1 kilobase pairs (kBp) in length; (ii) the extension cycle for the PCR reaction is about 0.5, 1, 2, 3, 4, or 5 seconds to about 60 seconds in duration, optionally wherein the PCR amplification product is at least about 0.5 or 1 kilobase pairs (kBp) in length.

24. The method of embodiment 22 or 23, wherein the sample comprises an inhibitory substance in an amount sufficient to cause a wild-type Taq polymerase comprising SEQ ID NO: 1 to fail to amplify the target nucleic acid in the PCR, optionally wherein the inhibitory substance is selected from the group consisting of chocolate, peanut butter, milk, seafood, meat, egg, plant material, blood, a blood fraction, urine, dye, soil, soil extract, humic acid, guanidinium thiocyanate (GITC), and ethanol.

25. The method of any one of embodiments 22, 23, or 24, wherein the PCR is real-time PCR, the assay mixture further comprises: (i) a non-specific DNA binding dye; or (ii) at least oligonucleotide which hybridizes to the amplification product, said oligonucleotide optionally comprising a fluorophore, and wherein amplifying the target nucleic acid comprises amplifying the target nucleic acid in the assay mixture in a real-time PCR.

26. The method of any one of embodiments 22 to 25, wherein the sample comprising the target nucleic is a clinical sample, optionally wherein the clinical sample comprises blood, serum, mucus, saliva, semen, or a combination thereof 27. The method of any one of embodiments 22-26, wherein; (i) the assay mixture comprises a sample comprising a target nucleic acid that is a target RNA, primers specific for the target RNA and/or cDNA transcribed from the target RNA, a buffer, and a reverse transcriptase activity; and (ii) the target RNA is amplified in a reverse transcriptase polymerase chain reaction (RT-PCR), optionally wherein the DNA polymerase comprises a polypeptide sequence having the amino acid sequence of SEQ ID NO: 6, 7, 8, 15, 16, 17, or a variant thereof, optionally wherein the assay mixture does not include a separate reverse transcriptase enzyme, optionally wherein the assay mixture does not include Mn$^{++}$ ion, optionally wherein the sample comprising a target RNA is not purified prior to addition to the assay mixture, and/or optionally wherein the assay mixture comprises an inhibitory substance in an amount sufficient to cause a wild type Taq polymerase to fail to amplify the target nucleic acid in the RT-PCR.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

Example 1. Generation and Selection of High Elongation Rate (HER) Mutants

Randomly mutagenized libraries of the Taq I gene encoding the full length wild-type TaqI DNA polymerase (SEQ ID NO: 1) were generated by using a conventional protocol for error-prone PCR in the presence of manganese for mutagenicity. The libraries were constructed in the pUC18 expression vector, harbored by the *R. coli* CT host strain, which has been optimized for protein expression. Each library contained around 1.0-1.5×10$^6$ clones, with 50-75% viable clones, as expected for the desired rate of mutagenesis.

The mutagenized Taq libraries were screened for the desired phenotype by a fast and simple real-time PCR-based technique. We utilized real-time PCR to screen the libraries for high-speed Taq mutants, giving some initial preference to this feature. The screening/selection was done with a BioRad CFX-96 cycler, in 96-well plate format, with a single clone per well. Several 2 kb long targets of the bacterial rRNA genes or plasmid DNA were used as templates. In order to select for high elongation rate (HER) mutants, we used progressively decreased annealing/extension times, going down to 1-2 seconds. Under such a high selective pressure only a few, or no successfully performing clones were observed per plate.

An alternative, in vivo mutagenesis approach to screening was also used. A "mutator" bacterial strain which introduces high number of errors during the DNA replication, was transformed with the same Taq mutant constructs used to generate our in vitro mutagenized libraries. After various times, 1-7 days of cells propagation, the isolated in vivo mutagenized plasmid DNAs were used to transform *R. coli* CT and BL-21 strains, followed by functional screening in our PCR procedure.

A total of around 5,000 clones were screened, ending with several promising candidates. To verify the high-speed performance, each selected clone was subjected to one or two additional screening rounds. After confirming the performance of the selected candidate, a small-scale enzyme prep was made of each candidate clone for further testing. The inhibition resistance (IR) feature of the isolated clones was tested with amplification of a 1 kb human target from increasing amounts of blood, 0-20%, and compared to the resistance of the starting enzyme constructs. The reverse transcriptase (RT) activity was tested in real-time RT-PCR of a 500 nt long target of the MS2 RNA phage.

Example 2. Mutation Analysis: Sequencing and Site-Directed Mutagenesis

Two-strand overlapping sequencing of the entire Taq ORF of the isolated clones was obtained after submitting plasmid DNA preps or purified PCR products to GENEWIZ, a company specialized in sequencing services. ABI Sequence Scan, BioEdit and BlastX software were used for analysis and alignment of the sequence data against the wild type Taq I entry in the GenBank (SEQ ID NO: 1). Among our best six selected mutant enzymes, A555 (SEQ ID NO: 3), A777 (SEQ ID NO: 4), G10 (SEQ ID NO: 5), F40 (SEQ ID NO: 6), F44 (SEQ ID NO: 7), and B66 (SEQ ID NO: 8), the first three showed relatively better, very high elongation speed, while the last three were performing better in RT-PCR (illustrated in the Figures). We also performed a saturation mutagenesis at codon 732, to test all possible 18 amino acid substitutions, and found that the lysine (K) improves the speed of the enzyme better than the original mutant with asparagine (N), therefore we kept the D732K change in the A777 enzyme. Sequencing data quality issues resulting from the GC-rich content and potential secondary structures in the Taq gene were resolved after trying several sequencing protocols and the use of multiple primers.

Figure 1A:
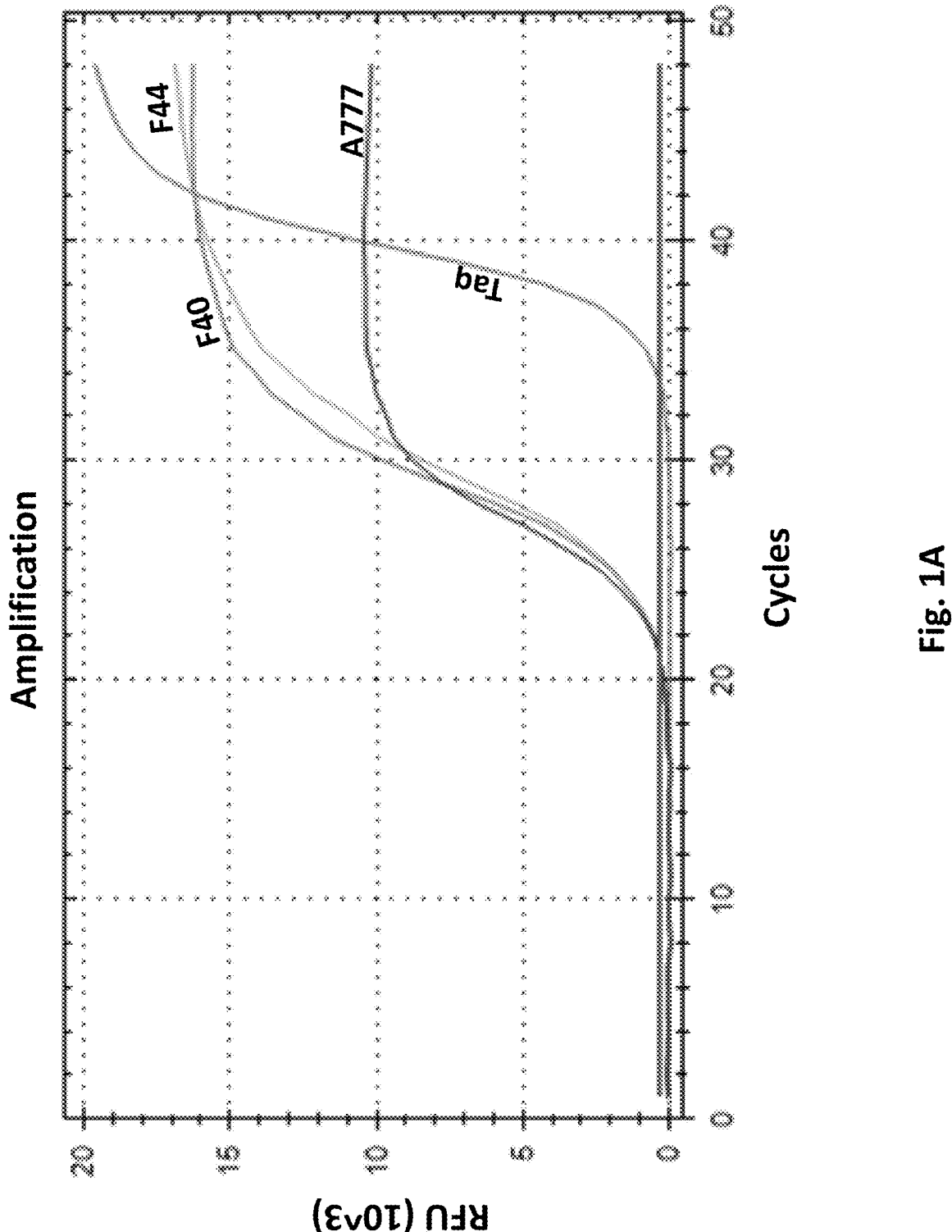
FIGS. 1A and 1B show fast PCR of long targets with novel high-speed Taq mutants.
Figure 1B:
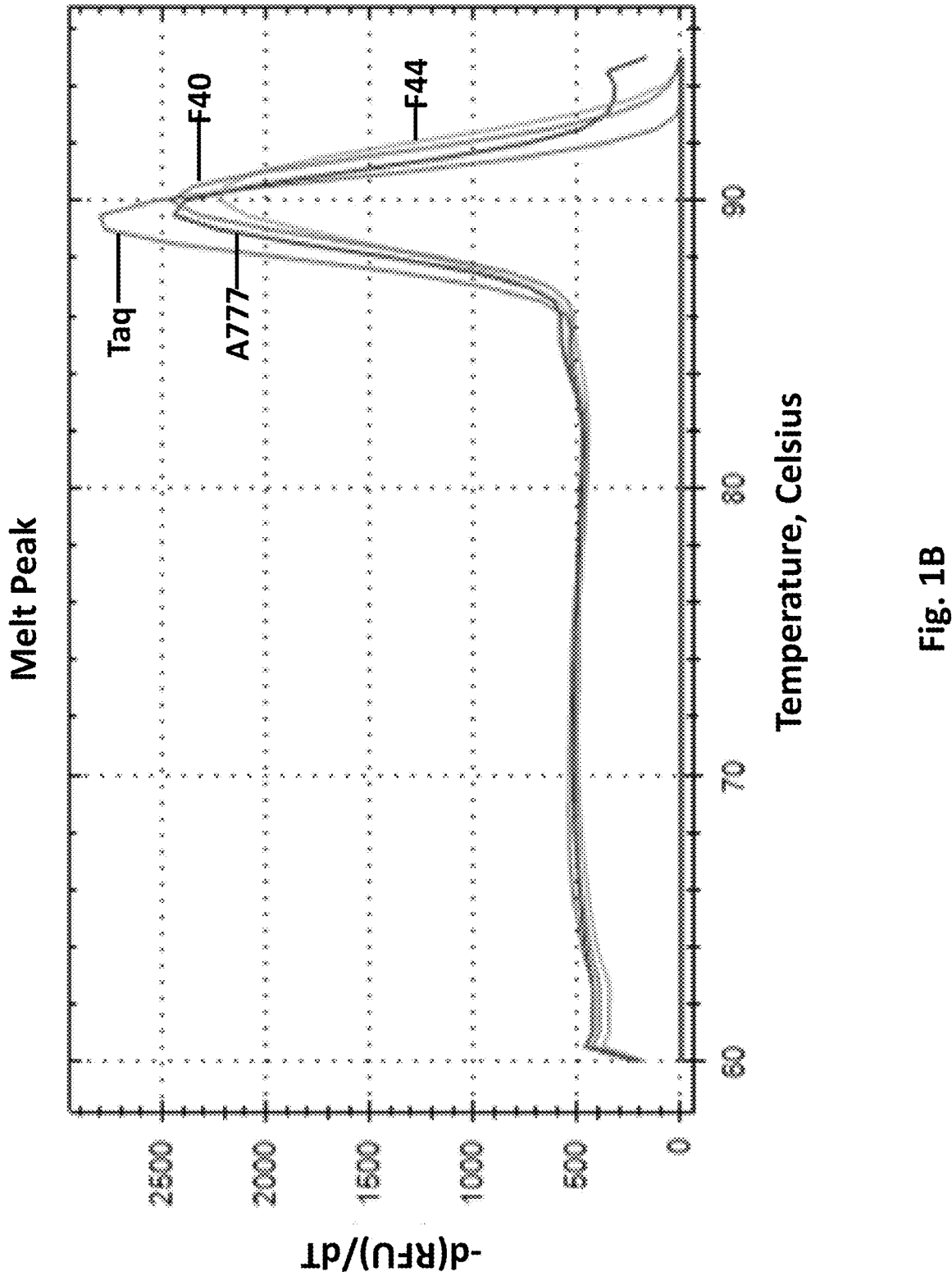
Figure 2A:
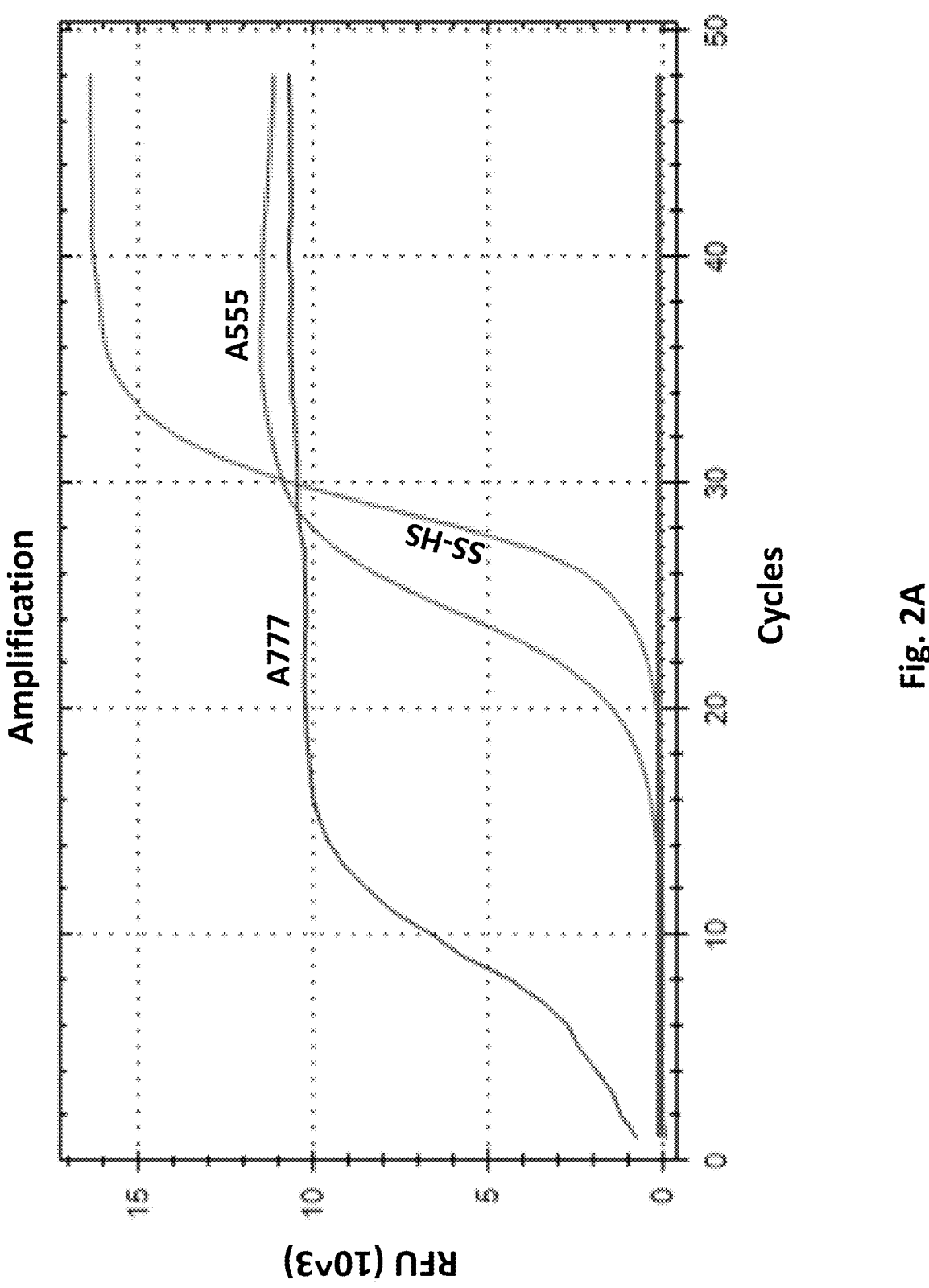
FIGS. 2A and 2B show a fast PCR comparison of A555 and A777 Taq mutants vs. SpeedSTAR™ HS Polymerase (Takara Bio).
Figure 2B:
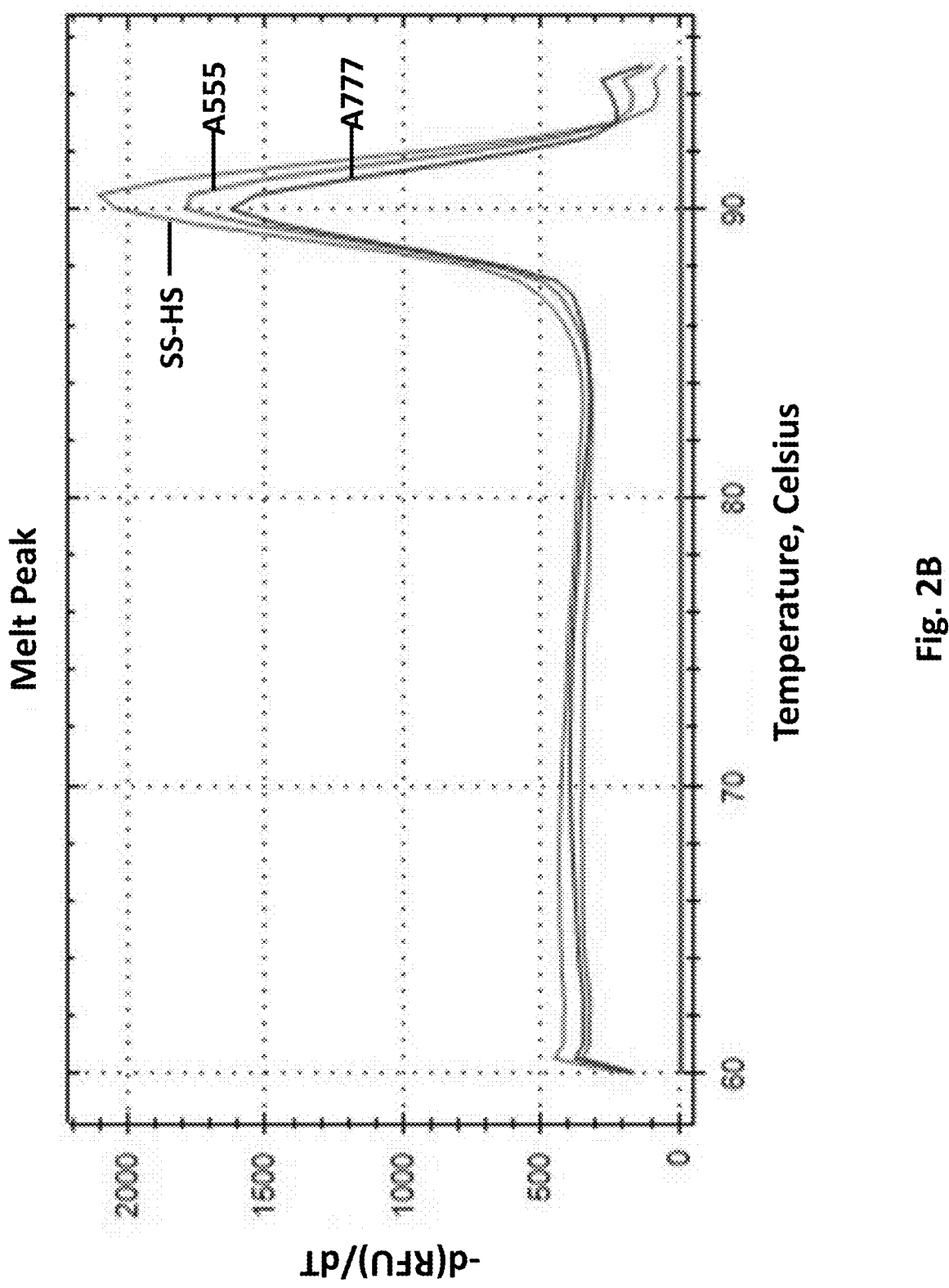
Figure 3A:
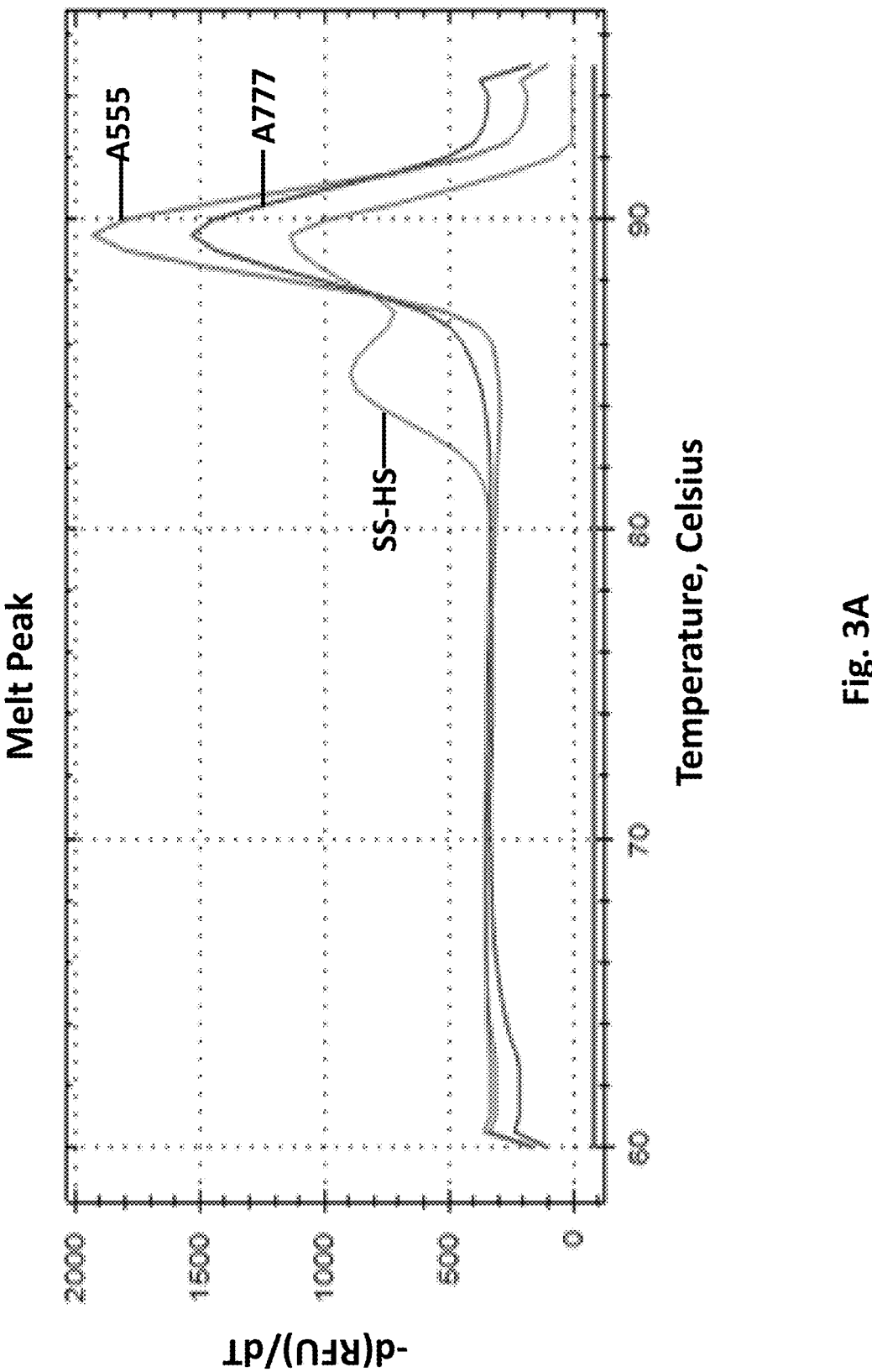
FIGS. 3A, 3B, 3C, and 3D show that the novel high-speed Taq DNA polymerase mutants can perform in extremely fast PCR.
Figure 3B:
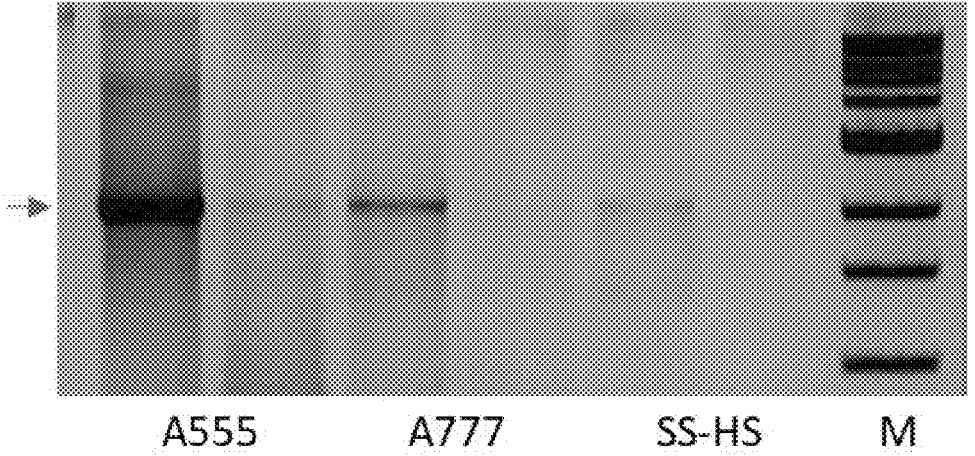
Figure 3C:
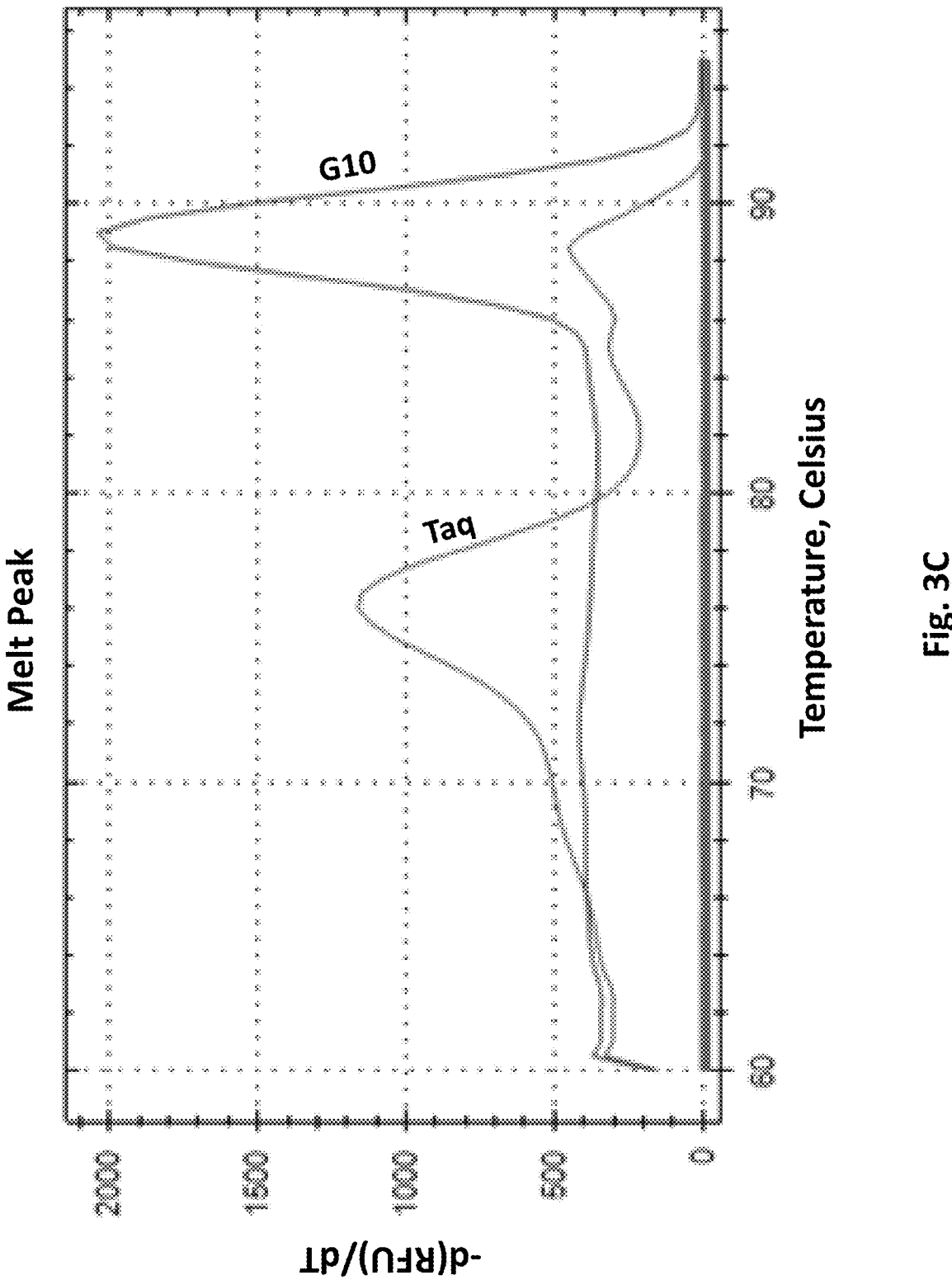
Figure 3D:
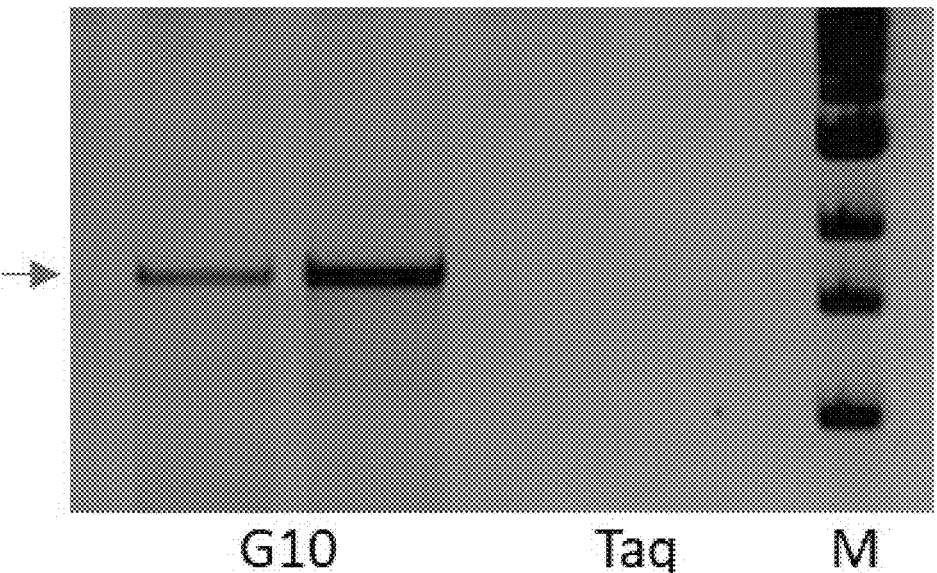
Figure 4A:
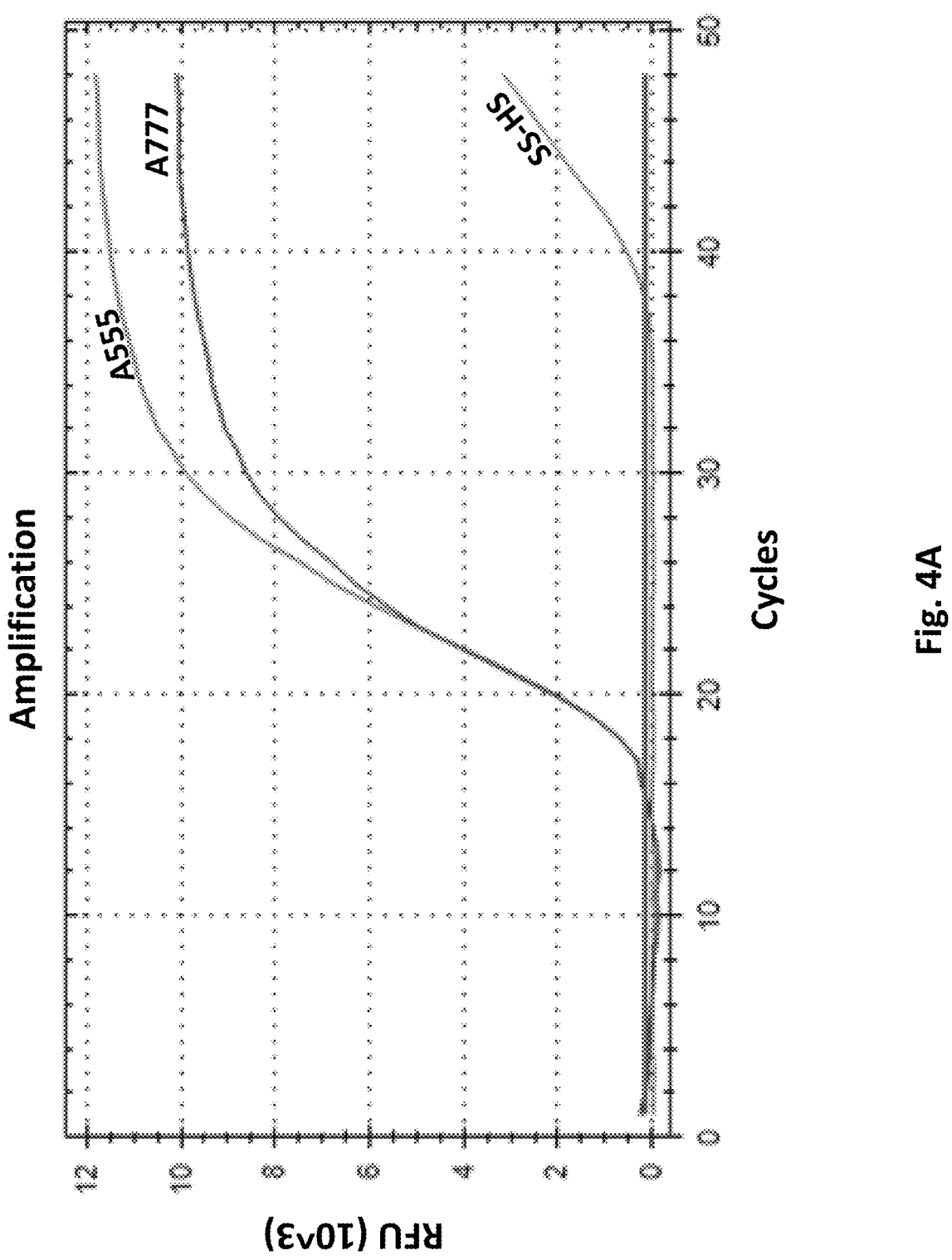
FIGS. 4A, 4B, and 4C show fast PCR in the presence of human serum for the A555 and A777 Taq mutants vs. SpeedSTAR™ HS polymerase.
Figure 4B:
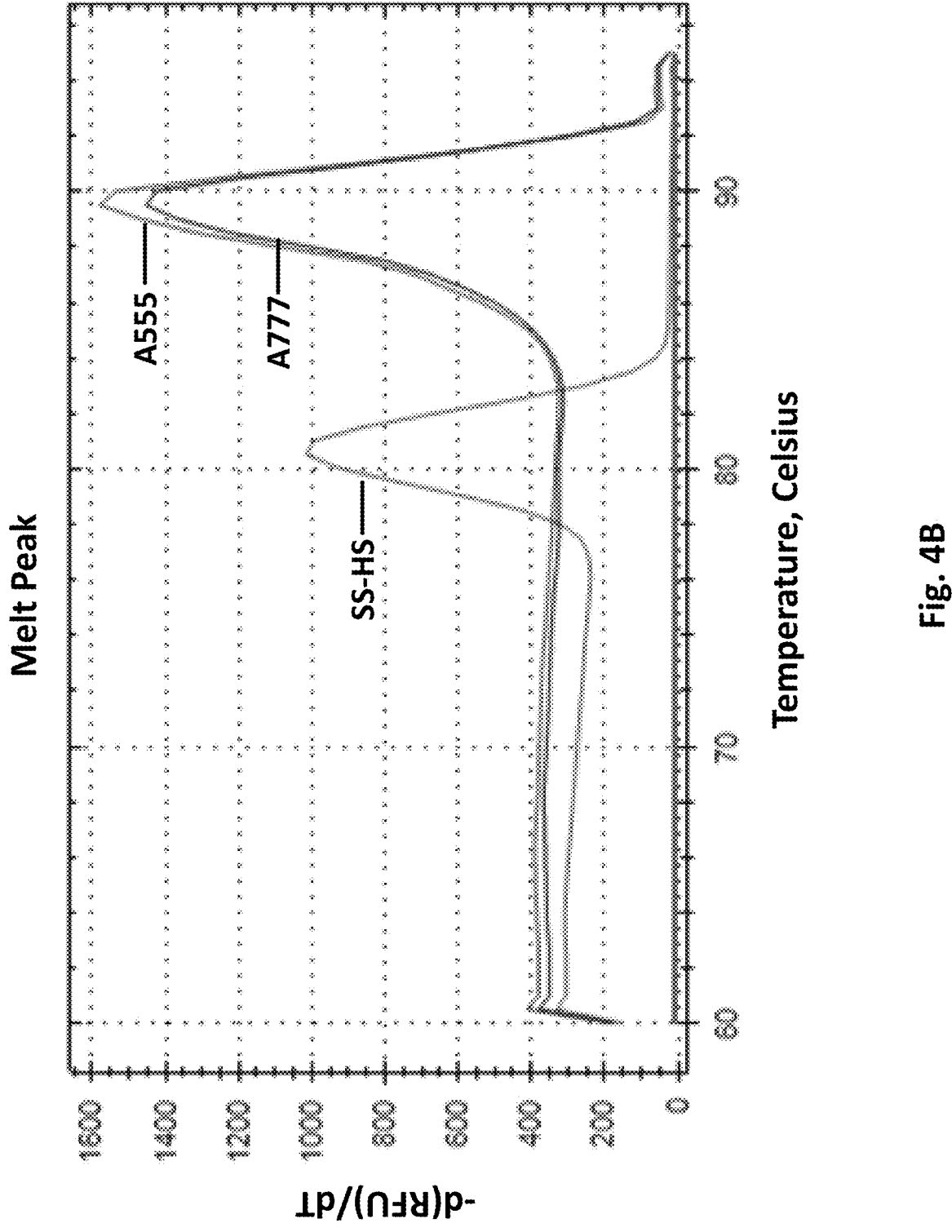
Figure 4C:
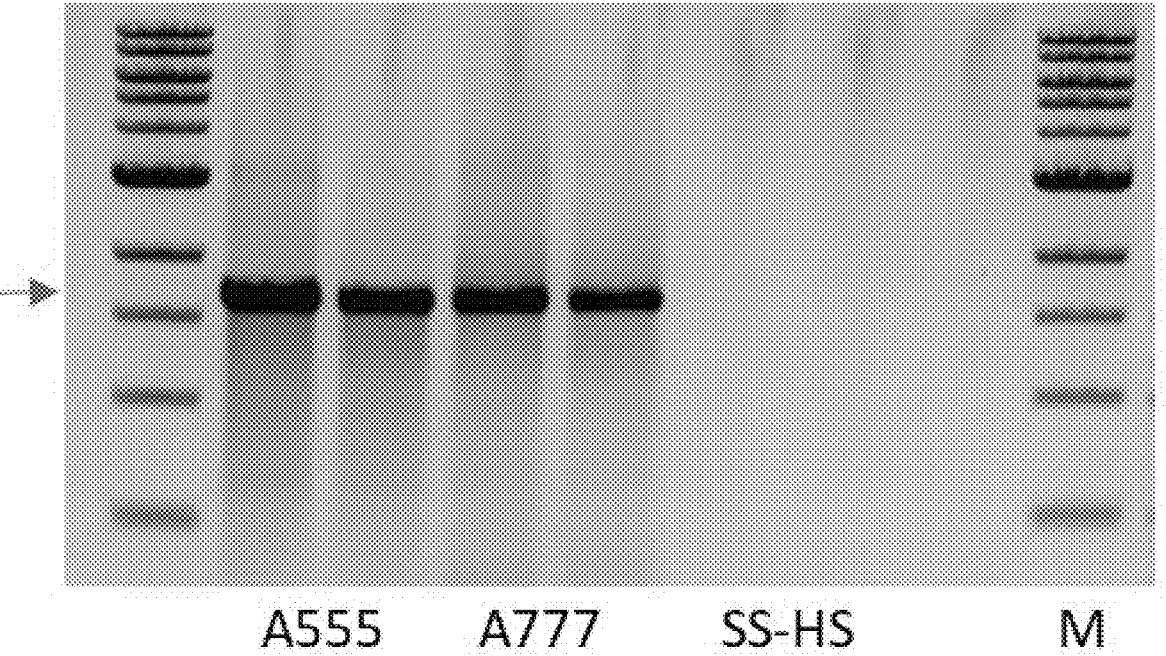

Example 3. Purification and Evaluation of the Selected Taq Mutant Enzymes, Buffer and Enhancer Optimization, and Implementation of the Novel Enzymes in Rapid Point-of-Care Microfluidic Devices The six best performing Taq mutants mentioned above were extensively purified with an established procedure for preparing commercial quality enzymes which is essentially as disclosed in U.S. Pat. No. 5,436,149, which is incorporated herein by reference in its entirety. Two of them, F40 and A777 turned out to be toxic to the host strain when overexpressed and required some optimization of the time and temperature of induction. They were also expressed in an alternative host strain, BL-21, but after careful optimization both strains were working equally well. After passing standard quality control (QC) tests, the purified enzymes were tested intensively for their HER, IR, and RT features. In order to demonstrate better the high speed of the enzymes, we used longer PCR targets, up to 2 kb. The main challenge in the fast PCR was the shortening of the annealing/extension time in a two-step cycling conditions. FIGS. 1-3 illustrate such tests and demonstrate that with an extension time reduced to 1-5 seconds per 2 kb targets, the A777 (SEQ ID NO: 4), A555 (SEQ ID NO: 3), F40 (SEQ ID NO: 6), and F44 (SEQ ID NO: 7) can outperform both the commercial wild type Taq (New England Biolabs) and the Speed-STAR™ HS (SS-HS) polymerase (Takara Bio USA San Jose, CA, USA). The SpeedSTAR™ HS (SS-HS) polymerase is advertised as a high-speed enzyme with an elongation rate of 5-10 sec/kilobase. These results indicate that the A777, A555, F40, and F44 variants have faster elongation rates than commercial PCR enzymes. Then we tested our novel enzymes in a double challenged PCR, combining extremely low extension times of 2-5 sec with the presence of two potent PCR inhibitors, blood or serum. In both cases the A555 (SEQ ID NO: 3) and A777 (SEQ ID NO: 4) mutants remained fully functional, while the control SS-HS polymerase failed (FIGS. 4-6). Next, we tested our mutant enzymes for their RT activity, using short HIV or HCV targets in serum samples, or a longer, 500 nt MS2 phage RNA target, and 1 sec extension time. FIG. 7 illustrates such a test, where the F44 (SEQ ID NO: 7) and B66 (SEQ ID NO: 8) mutants amplified efficiently the 500 nt target, while the SS-HS enzyme failed. In another series of tests, we used a commercial anti-Taq antibody, that reversibly blocks the enzyme at lower temps, to add the hot start (HS) feature to the new enzymes. FIG. 8 demonstrates that this approach works very well, and the fast mutants' performance in a hot start demanding PCR matches that of two commercial HS enzymes. We provided enzyme samples to Fluxergy (Irvine, CA, USA) for evaluation with their portable PCR devices, and they confirmed a good performance of the G10 (SEQ ID NO: 5) enzyme in direct detection of *Salmonella* in saliva samples. It appears that the new DNA polymerase mutant enzymes with improved performance in high-speed PCR of crude samples will be quite competitive in a variety of clinical applications.

---

What is claimed is:

1. A DNA polymerase comprising a polypeptide sequence having at least 95% sequence identity to positions 279 through 832 of SEQ ID NO: 1, and further comprising one or more amino acid substitutions selected from the group consisting of A391T, P752S, and combinations thereof, wherein all amino acid substitutions are relative to SEQ ID NO: 1.

2. The DNA polymerase of claim 1, wherein said polymerase further comprises one or more amino acid substitutions selected from the group consisting of D732N, D732R, D732K, K738R, E742R, E742K, A743R, A743K, E818V, A814T, and combinations thereof, wherein all amino acid substitutions are relative to SEQ ID NO: 1.

3. The DNA polymerase of claim 2, wherein said DNA polymerase comprises amino acid substitutions: (a) A391T; (b) D732N; (c) P752S; (d) E742R; (e) A743R; and (f) E818V, wherein all amino acid substitutions are relative to SEQ ID NO: 1.

4. The DNA polymerase of claim 3, wherein said DNA polymerase comprises the polypeptide sequence of SEQ ID NO: 3 or SEQ ID NO: 12.

5. The DNA polymerase of claim 3, wherein said DNA polymerase has polymerase activity in the presence of an inhibitory substance in an amount sufficient to cause a wild-type Taq polymerase comprising SEQ ID NO: 1 to fail to amplify a target nucleic acid in a polymerase chain reaction (PCR), wherein the inhibitory substance comprises one or more of chocolate, peanut butter, milk, seafood, meat, egg, plant material, blood, a blood fraction, urine, dye, soil, soil extract, humic acid, guanidinium thiocyanate (GITC), or ethanol.

6. The DNA polymerase of claim 3, wherein the DNA polymerase exhibits reverse transcriptase activity.

7. The DNA polymerase of claim 3, wherein the DNA polymerase: (i) has polymerase activity in the presence of an inhibitory substance in an amount sufficient to cause a wild-type Taq polymerase comprising SEQ ID NO: 1 to fail to amplify a target nucleic acid in a polymerase chain reaction (PCR), wherein the inhibitory substance comprises one or more of chocolate, peanut butter, milk, seafood, meat, egg, plant material, blood, a blood fraction, urine, dye, soil, soil extract, humic acid, guanidinium thiocyanate (GITC), or ethanol; (ii) exhibits reverse transcriptase activity; and (iii) exhibits an elongation rate of 0.5 to 4 or 5 seconds/kilobase.

8. The DNA polymerase of claim 1, wherein said DNA polymerase comprises a polypeptide sequence having at least 96%, 97%, 98%, or 99% sequence identity to positions 279 through 832 of SEQ ID NO: 1.

9. The DNA polymerase of claim 1, wherein said DNA polymerase comprises a polypeptide sequence having at least 95%, 96%, 97%, 98%, or 99% sequence identity to positions 1 through 832 of SEQ ID NO: 1.

10. The DNA polymerase of claim 1, wherein the DNA polymerase exhibits an elongation rate of 0.5 to 4 or 5 seconds/kilobase.

11. A recombinant DNA molecule comprising a polynucleotide encoding the DNA polymerase claim 1, wherein a heterologous promoter is operably linked to the polynucleotide.

12. A cell comprising the recombinant DNA molecule of claim 11.

13. A composition comprising the DNA polymerase of claim 1, wherein the composition further comprises at least one of an anti-Taq antibody, an anti-Taq monoclonal antibody, an anti-Taq aptamer, or a buffering agent.

14. A method of amplifying a target nucleic acid in a polymerase chain reaction (PCR) comprising: forming an assay mixture comprising a sample comprising a target nucleic acid, primers specific for the target nucleic acid, a buffer, and the DNA polymerase of claim 1; and amplifying the target nucleic acid in the assay mixture in a PCR to produce a PCR amplification product.

15. The method of claim 14, wherein: (i) the extension cycle for the PCR reaction is 1 or 2 to 3, 4, or 5 seconds in duration and wherein the PCR amplification product is at least 0.5 or 1 kilobase pairs (kBp) in length; (ii) the extension cycle for the PCR reaction is at least 0.5, 1, 2, 3, 4, or 5 seconds in duration and wherein the PCR amplification product is at least 0.5 or 1 kilobase pairs (kBp) in length; or (iii) the extension cycle for the PCR reaction is 0.5, 1, 2, 3, 4, or 5 seconds to 60 seconds in duration and wherein the PCR amplification product is at least 0.5 or 1 kilobase pairs (kBp) in length.

16. The method of claim 14, wherein the DNA polymerase comprises amino acid substitutions A391T, D732N, P752S, A743R, and E818V, and wherein the sample comprises an inhibitory substance in an amount sufficient to cause a wild-type Taq polymerase comprising SEQ ID NO: 1 to fail to amplify the target nucleic acid in the PCR, optionally wherein the inhibitory substance is selected from the group consisting of chocolate, peanut butter, milk, seafood, meat, egg, plant material, blood, a blood fraction, urine, dye, soil, soil extract, humic acid, guanidinium thiocyanate (GITC), and ethanol.

17. The method of claim 14, wherein the PCR is real-time PCR, wherein the assay mixture further comprises: (i) a non-specific DNA binding dye; or (ii) at least one oligonucleotide which hybridizes to the amplification product, said oligonucleotide optionally comprising a fluorophore, and wherein amplifying the target nucleic acid comprises amplifying the target nucleic acid in the assay mixture in a real-time PCR.

18. The method of claim 14, wherein the DNA polymerase comprises amino acid substitutions A391T, D732N, P752S, A743R, and E818V and wherein the sample comprising the target nucleic is a clinical sample, optionally wherein the clinical sample comprises blood, serum, mucus, saliva, semen, or a combination thereof.

19. The method of claim 14, wherein: (i) DNA polymerase comprises amino acid substitutions A391T, D732N, and P752S; (ii) the assay mixture comprises a sample comprising a target nucleic acid that is a target RNA, primers specific for the target RNA and/or cDNA transcribed from the target RNA, a buffer, and a reverse transcriptase activity; and (iii) the target RNA is amplified in a reverse transcriptase polymerase chain reaction (RT-PCR).

20. The method of claim 19, wherein the DNA polymerase comprises amino acid substitutions A391T, D732N, P752S, A743R, and E818V, wherein the assay mixture does not include a separate reverse transcriptase enzyme and/or wherein the assay mixture does not include $Mn^{++}$ ion, optionally wherein the sample comprising a target RNA is not purified prior to addition to the assay mixture, and/or optionally wherein the assay mixture comprises an inhibitory substance in an amount sufficient to cause a wild type Taq polymerase to fail to amplify the target nucleic acid in the RT-PCR.

* * * * *